United States Patent
Onchi et al.

(10) Patent No.: US 6,794,528 B2
(45) Date of Patent: Sep. 21, 2004

(54) PHOSPHORUS COMPOUND

(75) Inventors: Yoko Onchi, Himeji (JP); Ikuo Takahashi, Kobe (JP)

(73) Assignee: Daicel Chemical Industries, Ltd., Osaka (JP)

( * ) Notice: Subject to any disclaimer, the term of this patent is extended or adjusted under 35 U.S.C. 154(b) by 125 days.

(21) Appl. No.: 10/018,971

(22) PCT Filed: Apr. 20, 2001

(86) PCT No.: PCT/JP01/03423
§ 371 (c)(1),
(2), (4) Date: Dec. 26, 2001

(87) PCT Pub. No.: WO01/81356
PCT Pub. Date: Nov. 1, 2001

(65) Prior Publication Data
US 2003/0109736 A1 Jun. 12, 2003

(30) Foreign Application Priority Data

| Apr. 26, 2000 | (JP) | 2000-125777 |
| Apr. 26, 2000 | (JP) | 2000-125778 |
| Apr. 26, 2000 | (JP) | 2000-125779 |
| Aug. 17, 2000 | (JP) | 2000-247140 |
| Nov. 7, 2000 | (JP) | 2000-339664 |

(51) Int. Cl.$^7$ .............. C07C 9/02; C07C 68/74
(52) U.S. Cl. .............. 558/70; 560/116

(56) References Cited

U.S. PATENT DOCUMENTS 3,947,423 A   3/1976   Hills

FOREIGN PATENT DOCUMENTS

| EP | 0 116 200 A1 | 8/1984 |
| JP | 49-10124 b | 3/1974 |
| JP | 51-19858 B2 | 6/1976 |
| JP | 57-55947 A | 4/1982 |
| JP | 58-187451 A | 11/1983 |
| JP | 2-18336 B2 | 4/1990 |
| JP | 3-14072 B2 | 2/1991 |
| JP | 5-1079 A | 1/1993 |
| JP | 9-286910 A | 11/1997 |
| JP | 11-35833 A | 2/1999 |
| WO | 97/31925 A1 | 9/1997 |

OTHER PUBLICATIONS

Ramos et al., Tetrahedron Lett., 1985, vol. 26 No. 48, pp. 5895–5898.
Jina et al., Biochemistry, 1990, vol. 29, No. 21, pp. 5203–5209.
Bartlett, et al., J. Am. Chem. Soc., 1978, vol. 100., No. 15, pp. 4852–4858.
Simons, Jr., J. Am. Chem. Soc., 1974, vol. 96 No. 20, pp. 6492–6498.
Kosolapoff et al., Wiley–interscience, 1973 vol. 6.

Primary Examiner—Paul J. Killos
(74) Attorney, Agent, or Firm—Birch, Stewart, Kolasch & Birch, LLP

(57) ABSTRACT

The phosphorus-containing compound of the present invention is represented by the following formula (I), (II) or (III):

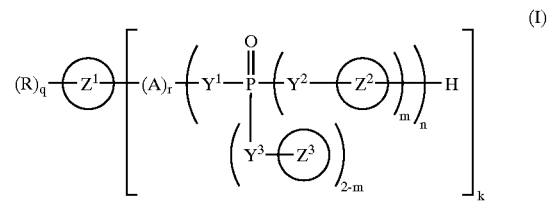

(I)

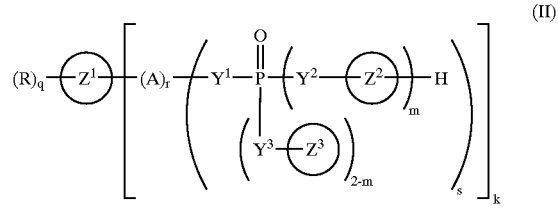

(II)

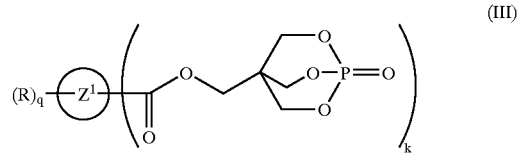

(III)

wherein $Z^1$, $Z^2$ and $Z^3$ each represents a cycloalkane, a cycloalkene, a polycyclic aliphatic hydrocarbon or an aromatic hydrocarbon rings which may have a substituent; R represents a halogen atom, a hydroxyl, a carboxyl, a halocarboxyl(haloformyl), an alkyl, an alkoxy, an alkenyl or an aryl groups; A represents a polyvalent group corresponding to an alkane; $Y^1$, $Y^2$ and $Y^3$ each represents —O—, —S— or —NR$^1$—, wherein $R^1$ represents a hydrogen atom or an alkyl group; k is an integer of 1 to 6; m is an integer of 0 to 2; n is an integer of not less than 1; q is an integer of 0 to 5; r is 0 or 1; and S is an integer of 1 to 4.

The phosphorus-containing compound is excellent in heat resistance and is useful as flame retardants, plasticizers, or stabilizers.

35 Claims, 6 Drawing Sheets

PHOSPHORUS COMPOUND

This application is the national phase under 35 U.S.C. §371 of PCT International Application No. PCT/JP01/03423 which has an International filing date of Apr. 20, 2001, which designated the United States of America.

TECHNICAL FIELD

The present invention relates to a phosphorus-containing compound useful as additives (in particular, flame retardants, plasticizers, stabilizers, etc) for various materials (e.g., compositions including hot-melt adhesives, thermosensitive tackifiers, delayed tack adhesives, image-receiving materials for forming an image by thermal transfer, photosensitizers for color photography, meltable inks for ink jet, shock-absorbing materials, pencil leads, and so on), further for organic compounds, particularly organic polymer compounds (e.g., vinyl chloride resins), lubricants, and heat transfer medium, etc, and relates to a process for producing the same. The phosphorous-containing compound is particularly useful as flame retardants, plasticizers, stabilizers, and the like.

BACKGROUND ART

Conventionally, organic polymers are molded or formed, with adding additives such as flame retardant, stabilizer in order to impart flame retardancy and stability to the organic polymers. Such additives are exemplified inorganic compounds, phosphorus-containing compounds (e.g., aromatic phosphoric esters (phosphates), phosphorus-containing aliphatic condensed compounds), halogen-containing compounds (e.g., organic halogen compounds, halogen-containing organic phosphorus compound). Among these additives, the halogen-containing compounds can impart high flame retardancy. Typical halogen-containing compounds include, for example, tetrabromo-diphenylether, tetrabromo-bisphenol A, tri(dichloropropyl)phosphate, and tri(dibromopropyl)phosphate.

The halogen-containing compounds are, however, thermally decomposed under a resin-molding process to generate a hydrogen halide, and so the hydrogen halide not only corrodes a metal mold and deteriorates characteristics of resins but also causes the working environment worse. Further, poisoned gases (hydrogen halides) generated by combustion of the halogen-containing compounds affect human bodies and environments adversely.

Meanwhile, among non-halogenous series additives, since inorganic compounds such as metal hydroxide (e.g., magnesium hydroxide, aluminum hydroxide) and metal oxide (e.g., antimony oxide, alumina) have a low flame retardability, large amount of inorganic compounds is required in order to obtain a desired flame retardancy. Therefore, the properties of resin are liable to be deteriorated.

Moreover, as non-halogenous additives expressing relatively high flame-retardantability, aromatic phosphoric esters (phosphates) such as triphenylphosphate (hereinafter, occasionally abbreviated as TPP) and tricresylphosphate are used. In particular, since TPP shows excellent flame retardancy, TPP is generally used. However, the volatility of TPP is high, and TPP is volatilized in a resin composition-molding process, to contaminate metal with deteriorating the external appearance of the molded articles.

Further, even though the above mentioned halogen-series additives and non-halogen-series additives are used in combination, flame-retardability of the articles is still insufficient.

Incidentally, Japanese Patent Publication No. 19858/1976 (JP-51-19858B), Japanese Patent Publication No. 18336/1990 (JP-2-18336B) and Japanese Patent Application Laid-Open No. 1079/1993 (JP-5-1079A) disclose condensed organic phosphorus compounds having low volatility in order to enhance flame retardancy for a variety of resins (e.g., polyester resins, polyamide resins, polycarbonate resins). Particularly, Japanese Patent Publication No. 19858/1976 (JP-51-19858B) discloses a method of producing the condensed phosphate mentioned above by reacting arylene-diol and diarylphosphochloridate. However, although heat resistance of these condensed phosphates is more excellent than that of TPP, it is difficult to impart high flame retardancy to resins.

Incidentally, Japanese Patent Application Laid-Open No. 55947/1982 (JP-57-55947A) discloses a halogen-containing resin composition obtained by adding a salt of organic acid with zinc, a salt of organic acid with Group IIa metal, an epoxy compound and/or an organic phosphate compound, and a specific organic phosphate compound to a halogen-containing resin, which is excellent in stability (particularly, stability of weather resistance). As the organic phosphate compounds, there are disclosed phosphoric esters (phosphates) of divalent or trivalent alcohols. The divalent or trivalent alcohols include ethylene glycol, triethylene glycol, cyclohexanediol, 1,4-phenyldimethanol, hydrogenated bisphenol.

Moreover, bicyclo phosphate compounds are disclosed in many publication, for example, ORGANIC PHOSPHOROUS COMPOUNDS vol. 6 (a Division of John Wiley & Sons. Inc.). Further, Japanese Patent Publication No. 14072/1991 (JP-3-14072B), Japanese Patent Application Laid-Open No. 35833/1999 (JP-11-35833A), Japanese Patent Application Laid-Open No. 286910/1997 (JP-9-286910A) and Japanese Patent Application Laid-Open No. 187451/1986 (JP-58-187451A) also disclose a variety of bicyclo phosphate compounds, and utilization of these compounds as an additive (e.g., flame retardant) for various resins. However, the effect (e.g., flame-retardant effect) of the compounds is not sufficient yet.

It is an object of the present invention to provide a novel phosphorus-containing compound excellent in heat resistance and useful as flame retardant, plasticizer or stabilizer.

It is another object of the present invention to provide a phosphorus-containing compound having low volatility and capable of imparting high flame retardancy to resins.

It is still another object of the present invention to provide a process for producing a phosphorus-containing compound capable of imparting high flame retardancy to resins, with high yield and high purity by simple manner.

DISCLOSURE OF INVENTION

The inventors of the present invention made Intensive studies to achieve the above objects and finally found that a phosphorus-containing compound having a specific ring structure remarkably improves flame retardancy of resins and is useful as plasticizer, stabilizer, etc. The present invention was accomplished based on the above findings.

That is, the phosphorus-containing compound of the present invention is represented by the following formula (I), (II) or (III):

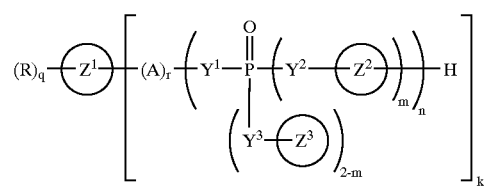 (I)

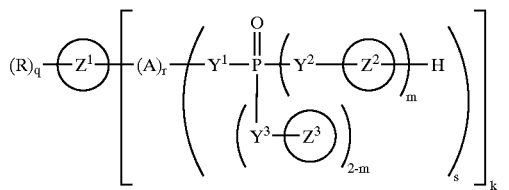 (II)

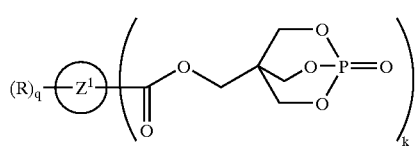 (III)

wherein $Z^1$, $Z^2$ and $Z^3$ are the same or different, each representing a cycloalkane ring, a cycloalkene ring, a polycyclic aliphatic hydrocarbon ring or an aromatic hydrocarbon ring, in which the rings may have a substituent; R represents a halogen atom, a hydroxyl group, a carboxyl group, a halocarboxyl(haloformyl) group, an alkyl group, an alkoxy group, an alkenyl group or an aryl group; A represents a polyvalent group corresponding to an alkane: $Y^1$, $Y^2$ and $Y^3$ are the same or different, each representing —O—, —S— or —$NR^1$— wherein $R^1$ represents a hydrogen atom or an alkyl group;

k represents an integer of 1 to 6; m represents an integer of 0 to 2; n represents an integer of not less than 1; q represents an integer of 0 to 5; r represents 0 or 1; s represents an integer of 1 to 4; and provided that when $Z^1$ is a cyclohexane ring, q is 0, and k is 1, factor r for A is 1; when $Z^1$ is a cyclohexane ring, q is 0, and k is 2 to 6, at least one of plural factors r for A is 1; and when $Z^1$ is a benzene ring and k is 1, the factor r for A is 1; when $Z^1$ is a benzene ring and k is 2 to 6, at least one of plural factors r for A is 1.

The rings $Z^1$, $Z^2$ and $Z^3$ each may be an aliphatic dicyclic hydrocarbon ring (e.g., a norbornane ring) or an aliphatic tricyclic hydrocarbon ring (e.g., an adamantane ring, a tricyclo[5.2.1.0$^{2,6}$]decane ring), or a benzene ring. In the formula (I), the R may be a halogen atom, a hydroxyl group, a $C_{1-4}$alkyl group, or a $C_{1-4}$alkoxy group. The each $Y^1$, $Y^2$ and $Y^3$ may represents —O—. The k may be 1 or 2, and n may be 1, and q may be 0 to 2. The phosphorus-containing compound represented by the formula (I), (II) or (III) may be a compound represented by the following formula (Ia), (Ib), (Ic), (Id), (Ie), (If), (IIa), or (IIIa):

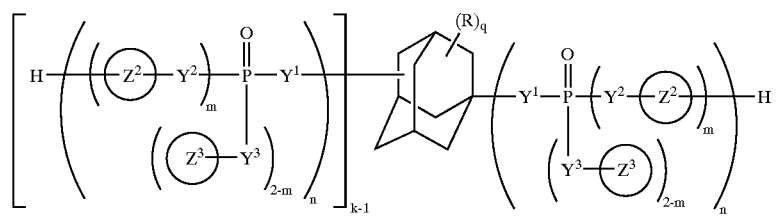 (Ia)

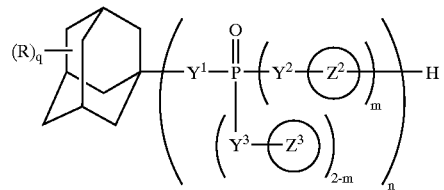 (Ib)

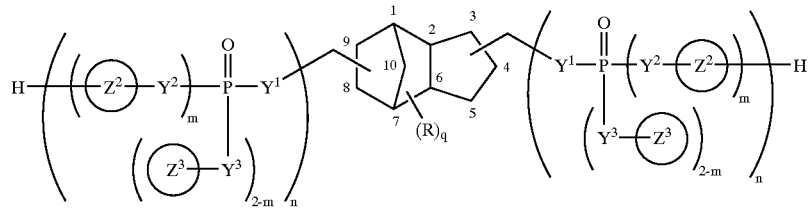 (Ic)

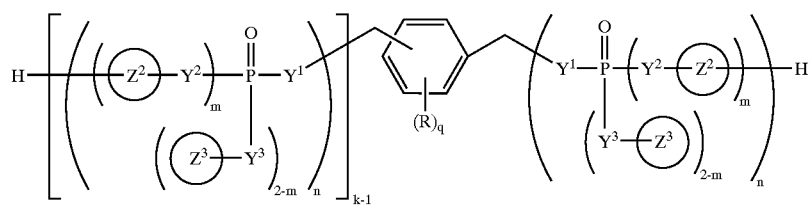 (Id)

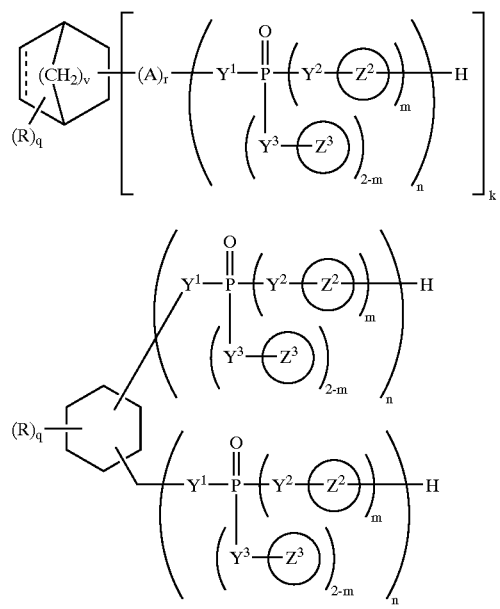

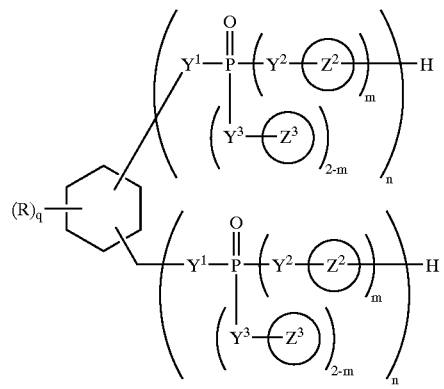

wherein the following structure $$\mathrel{\overline{\text{------}}}$$ (30)

represents a single bond or a double bond; v is an integer of 0 to 2; $Z^2$, $Z^3$, R, $Y^1$, $Y^2$, $Y^3$, k, m, n, q, r and s have the same meanings as defined above.

The present invention also includes a process for producing the phosphorus-containing compound.

BEST MODE FOR CARRYING OUT THE INVENTION

Figure 1:
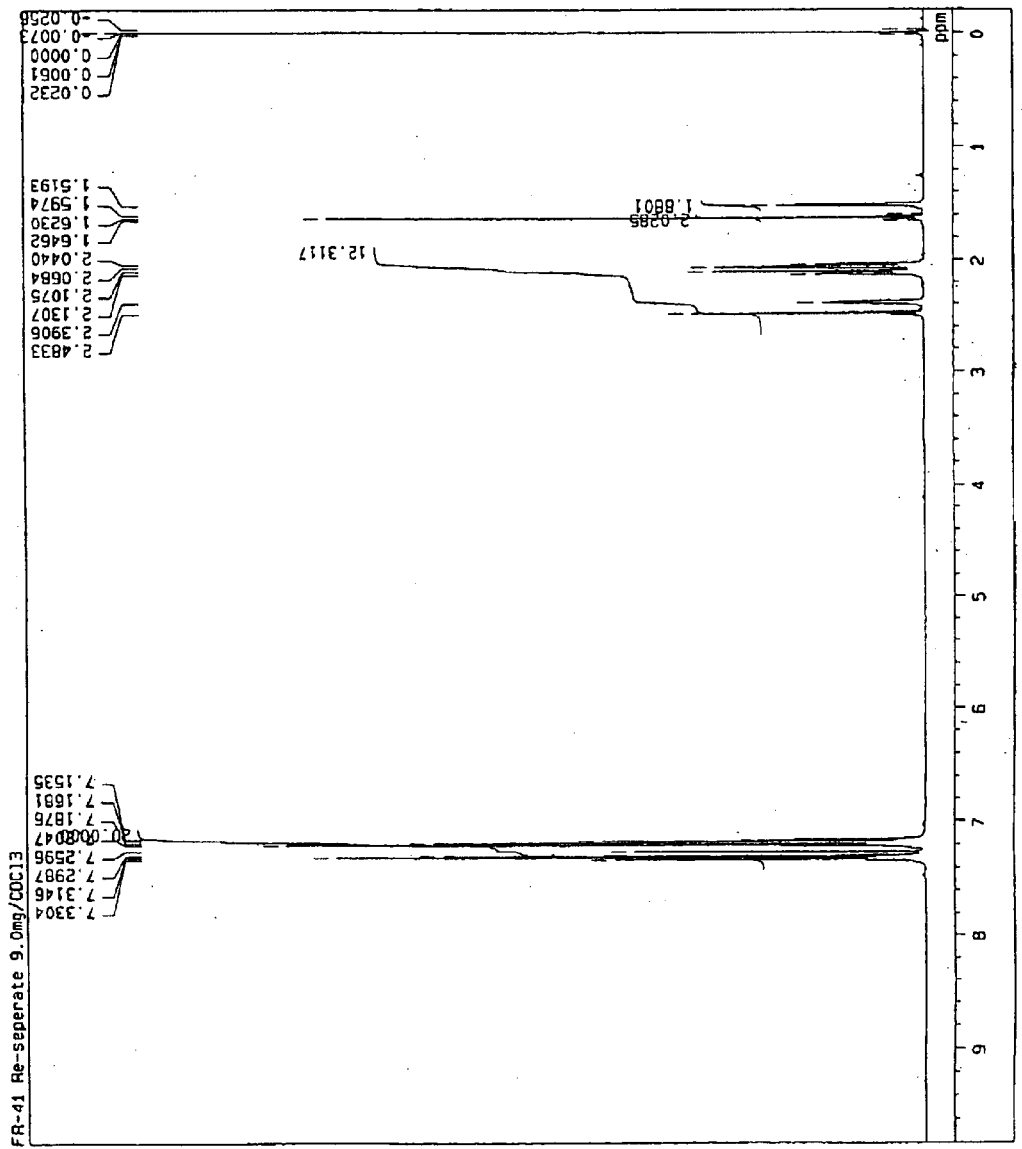
FIG. 1 is a $^1$H-NMR spectrum for the adamantylbis(diphenylphosphate) obtained in Example A1.

The phosphorus-containing compound of the present invention is represented by the following formulae (I), (II) or (III):

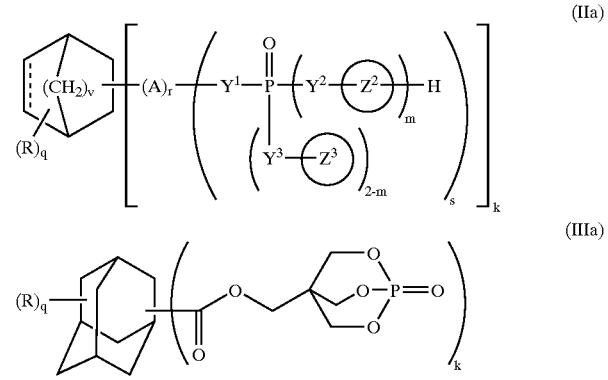

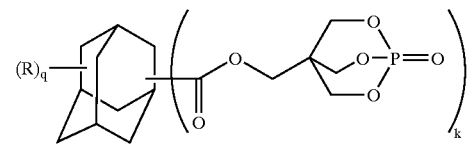

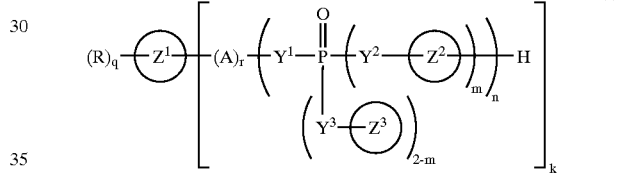

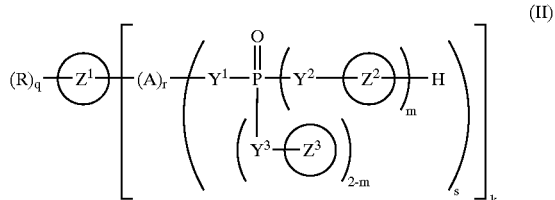

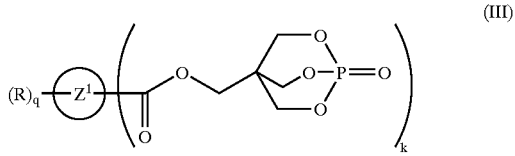

wherein $Z^1$, $Z^2$ and $Z^3$ are the same or different, each representing a cycloalkane ring, a cycloalkene ring, a polycyclic aliphatic hydrocarbon ring or an aromatic hydrocarbon ring, in which these rings may have a substituent; R represents a halogen atom, a hydroxyl group, a carboxyl group, a halocarboxyl group, an alkyl group, an alkoxy group, an alkenyl group or an aryl group; A represents a polyvalent group corresponding to an alkane; $Y^1$, $Y^2$ and $Y^3$ are the same or different, each representing —O—, —S— or —NR$^1$— wherein R$^1$ represents a hydrogen atom or an alkyl group.

As cycloalkane rings represented by $Z^1$, $Z^2$, and $Z^3$, there are exemplified C$_{4-20}$cycloalkane rings such as cyclobutane, cyclopentane, cyclohexane, cycloheptane, cyclooctane, cyclononane, cyclododecane, cyclopentadecane, and cyclooctadecane rings (preferably C$_{4-16}$cycloalkane rings, and more preferably C$_{4-12}$ cycloalkane rings). As cycloalkene rings, there are exemplified rings corresponding to the cycloalkane rings [(e.g., $C_{4-20}$cycloalkene rings such as cyclohexene ring and cyclooctene ring (preferably $C_{4-16}$cycloalkene rings, and more preferably $C_{4-12}$cycloalkene rings)].

As aliphatic polycyclic hydrocarbon rings represented by $Z^1$, $Z^2$ and $Z^3$, aliphatic crosslinked hydrocarbon rings and aliphatic condensed hydrocarbon rings are included.

As aliphatic crosslinked hydrocarbon rings, there may be dicyclic or bicyclic hydrocarbon rings such as pinane, bornane, norpinane, and norbornane rings; tricyclic hydrocarbon rings such as homobrendane, adamantane, tricyclo[5.2.1.0$^{2,6}$]decane, and tricyclo[4.3.1.1$^{2,5}$]undecane rings; tetracyclic hydrocarbon rings such as tetracyclo[4.4.0.1$^{2,5}$.1.$^{7,10}$]dodecane and perhydro-1,4-methano-5,8-methanonaphthalene rings, etc; hydrogenated compounds of dimers of diens [e.g., hydrogenated compounds of dimers of cycloalkadienes such as cyclopentadiene, cyclohexadiene and cycloheptadiene, including, e.g., perhydro-4,7-methanoindene; dimers of butadiene (vinyl cyclohexene) or hydrogenated compounds thereof; dimers of butadiene and cyclopentadiene (vinyl norbornene) or hydrogenated compounds thereof]. The preferred crosslinked-cyclic hydrocarbon rings include dicyclic rings such as norbornane ring, and tricyclic rings such as adamantane and tricyclo[5.3.1.0$^{2,6}$] decane rings, and the particularly preferred crosslinked-cyclic hydrocarbon rings are adamantane ring and tricyclo[5.2.1.0$^{2,6}$]decane ring.

As condensed cyclic hydrocarbon rings, there may be mentioned, for example, a 5- to 8-membered cycloalkane-condensed ring such as perhydronaphthalene ring (decalin ring), perhydroanthracene ring, perhydrophenanthrene ring, perhydroacenaphthene ring, perhydrofluorene ring, perhydroindene ring, and perhydrophenalene ring.

Examples of aromatic hydrocarbon rings include aromatic hydrocarbon rings having carbon numbers of 6 to 14 (preferably carbon numbers of 6 to 10) such as benzene ring and naphthalene ring. As the preferred aromatic hydrocarbon ring, there is exemplified benzene ring.

Halogen atoms represented by R include fluorine, chlorine, bromine, and iodine atoms. The preferred halogen atom is chlorine atom. As halocarboxyl groups, there are exemplified chlorocarboxyl group, bromocarboxyl group, and iodecarboxyl group. The preferred halocarboxyl group is chlorocarboxyl group.

Examples of alkyl groups include $C_{1-8}$alkyl groups such as methyl, ethyl, n-propyl, isopropyl, isobutyl, t-butyl, t-pentyl, hexyl, isooctyl, t-octyl, and 2-ethylhexyl groups (preferably $C_{1-6}$alkyl groups, more preferably $C_{1-4}$alkyl groups, and particularly methyl, ethyl, isopropyl, and t-butyl groups).

The alkyl groups may have a substituent. As the substituent, there may be exemplified various substituents, for example, $C_{6-18}$aryl groups such as phenyl group; halogen atoms (fluorine, chlorine, bromine or iodine atom); hydroxyl group; $C_{1-8}$alkoxy groups such as methoxy and ethoxy groups; carboxyl group; diaryl phosphoroxy groups such as diphenyl phosphoroxy group; cyano group; nitro group; and amino group. These substituents may be used singly or in combination.

The preferred substituent includes hydroxyl group, diaryl phosphoroxy group, and amino group. Incidentally, there is no particular restriction on numbers of the substituent, and the number of substituent is for example about 0 to 4, preferably about 0 to 3, and more preferably about 0 to 2.

More concretely, as alkyl groups substituted with hydroxyl group, there may be, for example, hydroxymethyl group, hydroxyethyl group, 3-, 2-, or 1-hydroxy-n-propyl group, 1- or 2-hydroxyisopropyl group, hydroxy-t-butyl group, 1,2-dihydroxyethyl group, and 1,2- or 2,3-dihydroxy-n-propyl group, and preferably hydroxymethyl group and 1,2-dihydroxyethyl group.

As alkyl groups substituted with diaryl phosphoroxy group, there are exemplified diphenylphosphoroxymethyl group, dicresylphosphoroxymethyl group, diphenylphosphoroxyethyl group, dicresylphosphoroxyethyl group, 3-, 2- or 1-diphenylphosphoroxy-n-propyl group, 3-, 2- or 1-dicresylphosphoroxy-n-propyl group, 1- or 2-diphenylphosphoroxyisopropyl group, 1- or 2-dicresyl phosphoroxyisopropyl group, diphenylphosphoroxy-t-butyl group, dicresylphosphoroxy-t-butyl group, 1,2-bis(diphenylphosphoroxy)ethyl group, 1,2-bis(dicresyl phosphoroxy)ethyl group, 1,2- or 2,3-bis(diphenyl phosphoroxy)-n-propyl group, and 1,2- or 2,3-bis(dicresylphosphoroxy)-n-propyl group, and preferably diphenylphosphoroxy methyl group and 1,2-bis(diphenyl phosphoroxy)ethyl group.

As alkyl groups substituted with amino group, there are exemplified aminomethyl group, aminoethyl group, 3-, 2-, or -amino-n-propyl group, 1- or 2-aminoisopropyl group, amino-t-butyl group, 1,2-diaminoethyl group, and 1,2- or 2,3-diamino-n-propyl group, and preferably aminomethyl group and 1,2-diaminoethyl group.

As alkoxy groups, there may be mentioned, for example, $C_{1-8}$alkoxy groups such as methoxy, ethoxy, n-propoxy, isopropoxy, isobutoxy, t-butoxy, t-pentyloxy, hexyloxy, isooctyloxy, t-octyloxy, and 2-ethylhexyloxy groups (preferably $C_{1-6}$alkoxy groups, more preferably $C_{1-4}$alkoxy groups, and particularly methoxy, ethoxy, isopropoxy, and t-butoxy groups).

As alkenyl groups, there may be, for example, vinyl, acryl, methacryl, isobutenyl, styrenyl, 1,3-butadienyl, and isoprenyl groups, and preferably vinyl group and methacryl group.

The aryl groups include, for example, $C_{6-14}$aryl groups such as phenyl group and naphthyl group, preferably $C_{6-10}$aryl groups, and more preferably phenyl group.

The aryl groups may have a substituent. As the substituent, there may be various substituents, for example, $C_{1-8}$alkyl groups such as methyl and ethyl groups (preferably $C_{1-6}$alkyl groups, and more preferably $C_{1-4}$alkyl groups); $C_{3-8}$cycloalkyl groups such as cyclohexyl group; $C_{6-18}$aryl groups such as phenyl group: $C_{6-12}$aryl-$C_{1-4}$alkyl groups such as benzyl group; halogen atoms (fluorine, chlorine, bromine or iodine atom); hydroxyl group; $C_{1-8}$alkoxy groups such as methoxy and ethoxy groups (preferably $C_{1-6}$alkoxy groups, and more preferably $C_{1-4}$alkoxy groups); carboxyl group; $C_{1-4}$alkoxycarbonyl groups such as methoxycarbonyl group: $C_{1-4}$alkyl-carbonyl groups such as methylcarbonyl group; $C_{6-12}$aryl-cabonyl groups; $C_{1-6}$acyloxy groups such as acetyloxy group; cyano group; nitro group; and sulfonyl group. These substituents may be used singly or in combination.

The preferred substituent includes alkyl group, hydroxyl group, alkoxy group, and halogen atom, and particularly alkyl group or alkoxy group.

Incidentally, there is no particular restriction on numbers of the substituent, and the number of substituent is for example about 0 to 4, preferably about 0 to 3, and more preferably about 0 to 2. The position of the substituent on benzene ring may be 2-, 3- or 4-position, 2,6- or 3,5-position, or 2,4,6-position, etc.

More concretely, as aryl groups substituted (modified) with alkyl group, there are exemplified mono, di or tri-$C_{1-}$ ₆alkylphenyl groups such as o-, m- or p-toluyl group, o-, m- or p-ethylphenyl group, o-, m- or p-n-octylphenyl group, o-, m- or p-(1,1,3,3-tetramethylbutyl)phenyl group, o-, m- or p-t-butylphenyl group, 2,6-, 2,5-, 2,4-, 2,3-, 3,5- or 3,4-xylyl group, 2,4,6- or 3,4,5-trimethylphenyl group, 2,6-, 2,5-, 2,4-, 2,3-, 3,5- or 3,4-di-t-butylphenyl group, and 2-methyl-6-t-butylphenyl group; and mono, di or tri-$C_{1-6}$alkylnaphthyl groups such as 2- or 3-methyl-1-naphthyl group and 1-, 3- or 4-methyl-2-naphthyl group.

The preferred alkyl-substituted aryl group includes mono, di or tri-$C_{1-4}$alkylphenyl groups such as o-, m- or p-toluyl group, p-ethylphenyl group, p-t-butyl group, p-(1,1-3,3-tetramethylbutyl)phenyl group, 2,4-, 3,4-, or 3,5-xylyl group, 2,4- or 2,6-di-t-butyl group, 2-methyl-6-t-butylphenyl group, and 2,4,6-trimethylphenyl group; and mono, di or tri-$C_{1-4}$alkylnaphthyl groups such as 2-methyl-1-naphthyl group.

As phenyl groups substituted (modified) with alkoxy group, there are may be, for example, mono, di or tri-$C_{1-6}$alkoxyphenyl groups such as o-, m- or p-methoxyphenyl group, o-, m- or p-ethoxyphenyl group, o-, m- or p-n-propoxyphenyl group, o-, m- or p-isopropoxyphenyl group, o-, m- or p-t-butoxyphenyl group, o-, m- or p-t-pentyloxyphenyl group, 2,3-, 2,4-, 2,5-, 2,6-, 3,4- or 3,5-dimethoxyphenyl group, 2,3-, 2,4-, 2,5- 2,6-, 3,4- or 3,5-diethoxyphenyl group, 2,3-, 2,4-, 2,5-, 2,6-, 3,4- or 3,5-diisobutoxyphenyl group, 2,3-, 2,4-, 2.5-, 2,6-, 3,4- or 3,5-di-tertiary-butoxyphenyl group, 2,3,4-, -2,4,6-, 3,4,5-, 2,3,5- or 2,3,6-trimethoxyphenyl group, and 2,3,4-, 2,4,6-, 3,4,5-, 2,3,5- or 2,3,6-triethoxyphenyl group.

The preferred alkoxy-substituted aryl group includes mono, di or tri-$C_{1-4}$alkoxyphenyl groups such as o-, m- or p-methoxyphenyl group, 2,6- or 3,5-dimethoxyphenyl group, and 3,4,5- or 2,4,6-trimethoxyphenyl group.

The rings $Z^1$, $Z^2$ and $Z^3$ may be substituted (modified) with a substituent R. Aliphatic policyclic hydrocarbon rings (particularly adamantane ring) substituted with the R (particularly alkyl group, alkoxy group, hydroxyl group, etc) includes the following rings.

Adamantane rings substituted with alkyl group [e.g., mono, di or tri-$C_{1-6}$alkyladamantane rings such as methyladamantane ring, ethyladamantane ring, n-propyladamantane ring, isopropyladamantane ring, dimethyladamantane ring, diethyladamantane ring, trimethyladamantane ring, and triethyladamantane ring (preferably mono or di-$C_{1-4}$alkyladamantane rings such as methyladamantane ring, dimethyladamantane ring, and diethyladamantane ring)].

Adamantane rings substituted with alkoxy group [e.g., mono, di or tri-$C_{1-6}$alkoxyadamantane rings such as methoxyadamantane ring, isobutoxyadamantane ring, n-propoxyadamantane ring, isopropoxy adamantane ring, dimethoxy adamantane ring, and diisobutoxy adamantane ring (preferably mono or di-$C_{1-4}$alkoxyadamantane rings such as dimethoxyadamantane ring and diisobutoxy adamantane ring)].

Adamantane rings substituted with hydroxyl group [e.g., mono, di or tri-hydroxyadamantane rings such as 2- or 3-hydroxyadamantane ring, 2,4- or 3,5-dihydroxyadamantane ring, and 3,5,7-trihydroxyadamantane ring (preferably di or tri-hydroxyadamantane rings such as 2- or 3-hydroxyadamantane ring, 3,5-dihydroxy adamantane ring, and 3,5,7-trihydroxyadamantane ring)].

As aromatic hydrocarbon rings (particularly benzene ring) substituted with the group R, there are exemplified substituted benzene rings corresponding to the above substituted phenyl group (e.g., mono, di or tri-$C_{1-4}$alkylbenzene rings, mono, di or tri-$C_{1-4}$alkoxybenzene rings).

The preferred rings $Z^1$, $Z^2$ and $Z^3$ are aliphatic dicyclic or tricyclic hydrocarbon rings such as norbornane ring or adamantane ring, which may have a substituent (e.g., hydroxyl group, halogen atom, $C_{1-8}$alkyl groups, $C_{1-8}$alkoxy groups), or benzene ring which may have the substituent. Moreover, the preferred rings $Z^1$, $Z^2$ and $Z^3$ may be $C_{6-12}$cycloalkane ring such as cyclohexane ring which may have a substituent (e.g., hydroxyl group, halogen atom, $C_{1-8}$alkyl groups, $C_{1-8}$alkoxy groups), or $C_{6-12}$cycloalkene rings such as cyclohexene ring which may have the substituent.

A represents polyvalent groups corresponding to alkanes (e.g., $C_{1-6}$alkanes such as methane, ethane, propane and butane, preferably $C_{1-4}$alkanes, and more preferably $C_{1-2}$alkanes), and usually represents divalent or trivalent groups. Incidentally, a bonding position of the polyvalent group may be at or on any carbon atom of the alkane.

Concerning to —$NR^1$— represented by $Y^1$, $Y^2$ and $Y^3$, as alkyl groups represented by the $R^1$, there are exemplified the above exemplified alkyl groups (e.g., $C_{1-6}$alkyl groups such as methyl, ethyl, propyl, and butyl groups, preferably $C_{1-4}$alkyl groups, particularly methyl group or ethyl group). As the —$NR^1$— group, there are exemplified —$N(CH_3)$— and —$N(C_2H_5)$—. The preferred $Y^1$, $Y^2$ and $Y^3$ represent —O— or —$N(R^1)$—, and particularly —O—.

k is an integer of 1 to 6, and k may be different each other depending on the species of the ring Z. k is usually 1 to 3. n is an integer of not less than 1 (e.g., 1 to 5, preferably 1 to 3, and more preferably 1 to 2), and is usually 1. q is an integer of 0 to 5, usually about 0 to 3, and preferably about 0 to 2. s is an integer of 1 to 4, and is usually 2 to 4 when k is 1, and at least one of plural factors is 2 to 4 when k is 2 to 6.

Incidentally, species of units comprising the group A and the group $Z^2$ and/or $Z^3$ which are units corresponding to k may be different depending on the number of k. Moreover, each kind of units comprising the group $Y^1$ and phosphorus atom which are units corresponding to n or s may be different depending on the number of n or s. Further, kinds of R and A may be respectively different depending on the numbers of q and r.

Among phosphorus-containing compounds represented by the formula (I), (II) or (III), as typical compounds, there are exemplified (i) a phosphorus-containing compound in which, in the formula (I), $Z^1$ is adamantane ring, k is not less than 2, and r (the factor or coefficient for A) is 0 [a compound represented by the formula (Ia)]; (ii) a phosphorus-containing compound in which $Z^1$ is adamantane ring, k is 1, and r is 0 in the formula (I) [a compound represented by the formula (Ib)]; (iii) a phosphorus-containing compound in which, in the formula (I), $Z^1$ is tricyclo[5.2.1.0$^{2,6}$]decane ring, k is 2, n and r are 1, and A is methylene group [a compound represented by the formula (Ic)]; (iv) a phosphorus-containing compound in which $Z^1$ is benzene ring, r is 1, and A is methylene group [a compound represented by the formula (Id)]; (v) a phosphorus-containing compound in which, in the formula (I) or (II), $Z^1$ is a saturated alicyclic hydrocarbon ring such as cyclohexane ring and norbornane ring, or an unsaturated alicyclic hydrocarbon ring such as cyclohexene ring [a compound represented by the formula (Ie) or (IIa)]; (vi) a phosphorus-containing compound in which, in the formula (Ie), $Z^1$ is cyclohexane ring, k is 2, one of r is 1, and A is methylene group [a compound represented by the formula (If)]; and (vii) a phosphorus-containing compound in which $Z^1$ is adamantane ring in the formula (III) [a compound represented by the formula (IIIa)].

(i) Phosphorus-containing compounds represented by the formula (Ia):

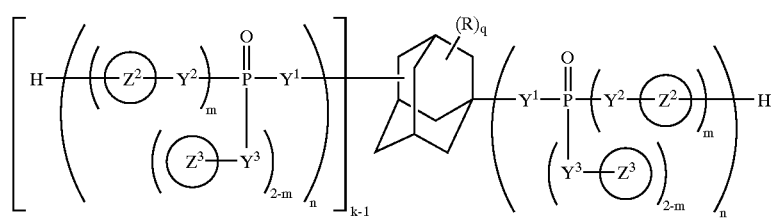

wherein $Z^2$, $Z^3$, R, $Y^1$, $Y^2$, $Y^3$, k, m, n and q have the same meanings as defined above.

In the formula (Ia), exemplified as the preferred ring $Z^2$ and $Z^3$ is a benzene ring or an adamantane ring. As the preferred R, there are exemplified hydrogen atom, halogen atom, hydroxyl group, $C_{1-6}$alkyl group or $C_{1-6}$alkoxy group (particularly hydrogen atom or $C_{1-4}$alkyl group). The preferred group $Y^1$, $Y^2$ and $Y^3$ are —O— or —$NR^1$— ($R^1$ has the same meaning as defined above). Moreover, k is usually 2 to 4, and n is 1 to 3 (particularly 1). The ring $Z^2$ and $Z^3$ may have a substituent (e.g., the group R).

Among the compound represented by the formula (Ia), as typical compounds, there are exemplified the following compounds.

A phosphorus-containing compound in which the ring $Z^2$ and $Z^3$ each is a benzene ring which may have a substituent (e.g., $C_{1-4}$alkyl group, hydroxyl group), R is $C_{1-4}$alkyl group, the groups $Y^1$ to $Y^3$ are —O—, k is 2 to 4, n is 1, and q is 0 to 2 [e.g., adamantylbis, tris or tetrakis-(di$C_{6-10}$arylphosphate) such as adamantylbis(diphenylphosphate) [or adamantane-diyl-bis(diphenyl phosphate)], adamantyltris(diphenylphosphate), adamantyl tetrakis (diphenylphosphate), dimethyladamantylbis (diphenylphosphate), adamantylbis(dicresylphosphate), adamantyltris(dicresylphosphate), adamantyltetrakis (dicresylphosphate), and dimethyladamantylbis(dicresyl phosphate)].

A phosphorus-containing compound in which the ring $Z^2$ and $Z^3$ each is a benzene ring which may have a substituent (e.g., $C_{1-4}$alkyl group, hydroxyl group), R is $C_{1-4}$alkyl group, the groups $Y^1$ to $Y^3$ are —$NR^1$— ($R^1$ is hydrogen atom), k is 2 to 4, n is 1, and q is 0 to 2 [adamantylbis, tris or tetrakis-(di$C_{6-10}$arylphosphoramide) such as adamantylbis(diphenyl phosphoramide) [or adamantane-diyl-bis(diphenyl phosphinoylamino)], adamantyltris (diphenylphosphoramide), adamantyltetrakis (diphenylphosphoramide), dimethyladamantylbis(diphenyl phosphoramide), adamantylbis(dicresylphosphoramide), adamantyltris(dicresylphosphoramide), adamantyltetrakis (dicresyl phosphoramide), and dimethyladamantylbis (dicresyl phosphoramide)].

Particularly, as the preferred compound, there are exemplified adamantylbis(diphenylphosphate), dimethyl adamantylbis(diphenylphosphate), and adamantyltris (diphenylphosphate).

(ii) Compounds represented by the following formula (Ib)

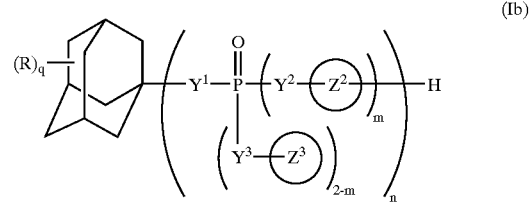

wherein $Z^2$, $Z^3$, R, $Y^1$, $Y^2$, $Y^3$, m, n and q have the same meanings as defined above.

In the formula (Ib), exemplified as the preferred ring $Z^2$ and $Z^3$ each is a benzene ring or an adamantane ring. As the preferred R, there are exemplified hydrogen atom, halogen atom, hydroxyl group, $C_{1-6}$alkyl group or $C_{1-6}$alkoxy group (particularly hydrogen atom, hydroxyl group, $C_{1-4}$alkyl group or $C_{1-4}$alkoxy group), and the preferred groups $Y^1$, $Y^2$ and $Y^3$ each is —O— or —$NR^1$—.

Among the compounds represented by the formula (Ib), as typical compounds, there are exemplified the following compounds.

A phosphorus-containing compound in which the ring $Z^2$ and $Z^3$ each is a benzene ring or an adamantane ring which may have a substituent (e.g., $C_{1-4}$alkyl group), R is $C_{1-4}$alkyl group, the groups $Y^1$ to $Y^3$ are —O—, k, m and n are 1, and q is 0 to 3 [e.g., adamantyldi$C_{6-10}$arylphosphates such as adamantyldiphenylphosphate and (dimethyladamantyl) diphenylphosphate, bis(adamantyl)$C_{6-10}$arylphosphates such as bis(adamantyl)phenylphosphate and bis (dimethyladamantyl)phenylphosphate, triadamantylphosphates such as tris(adamantyl)phosphate and tris (dimethyladamantyl)phosphate].

A phosphorus-containing compound in which the ring $Z^2$ and $Z^3$ each is a benzene ring or an adamantane ring which may have a substituent (e.g., $C_{1-4}$alkyl group), R is $C_{1-4}$alkyl group, the groups $Y^1$ to $Y^3$ are —$NR^1$— ($R^1$ is hydrogen atom), k, m and n are 1, and q is 0 to 2 [e.g., adamantyldi$C_{6-10}$arylphosphoramides such as adamantyl diphenylphosphoramide and dimethyladamantyldiphenyl phosphoramide, bis(adamantyl)$C_{6-10}$arylphosphoramides such as bis (adamantyl)phenylphosphoramide and bis (dimethyladamantyl)phenylphosphoramide, trisadamantylphosphoramide, tris(dimethyladamantyl) phosphoramide].

Particularly, adamantyldiphenylphosphate, dimethyladamantyldiphenylphosphate, and bis(adamantyl) phenylphosphate are preferred.

Incidentally, the compound of the formula (Ib) corresponds to a compound in which k is 1 in the formula (Ia).

(iii) Compounds represented by the following formula (Ic):

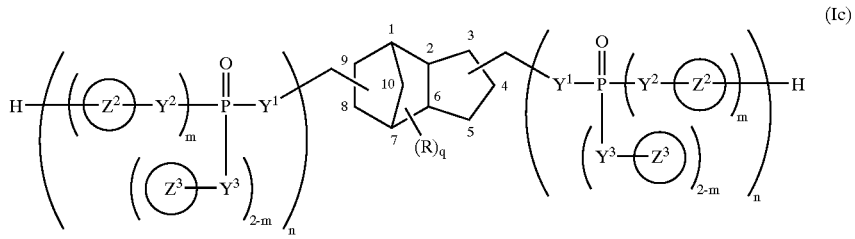

(Ic)

wherein $Z^2$, $Z^3$, R, $Y^1$, $Y^2$, $Y^3$, m, n and q have the same meanings as defined above.

In the formula (Ic), the preferred ring $Z^2$ and $Z^3$ each is a benzene ring, and the preferred R is halogen atom, hydroxyl group, $C_{1-6}$alkyl group or $C_{1-6}$alkoxy group. Moreover, the preferred groups $Y^1$, $Y^2$ and $Y^3$ are —O—.

Among the compound represented by the formula (Ic), as typical compounds, there are exemplified phosphorus-containing compounds in which the ring $Z^2$ and $Z^3$ each is a benzene ring which may have a substituent (e.g., $C_{1-4}$alkyl group, hydroxyl group), and the groups $Y^1$ $Y^2$ and $Y^3$ are —O— [e.g., bis[(di$C_{6-10}$arylphosphoroxy)methyl]tricyclo[5.2.1.0$^{2,6}$]decane such as 3,8-, 3,9-, 4,8- or 4,9-bis[(diphenylphosphoroxy)methyl]tricyclo[5.2.1.0$^{2,6}$]decane, 3,8-, 3,9-, 4,8- or 4,9-bis[(dixylyl phosphoroxy)methyl]tricyclo[5.2.1.0$^{2,6}$]decane, 3,8-, 3,9-, 4,8- or 4,9-bis[(ditoluylphosphoroxy)methyl]tricyclo[5.2.1.0$^{2,6}$]decane, and 3,8-, 3,9-, 4,8- or 4,9-bis[(dicresylphosphoroxy)methyl]tricyclo[5.2.1.0$^{2,6}$]decane].

As the preferred compound, there is exemplified 3,8-, 3,9-, 4,8- or 4,9-bis[(diphenylphosphoroxy)methyl]tricyclo[5.2.1.0$^{2,6}$]decane.

Moreover, the compound represented by the formula (Ic) includes isomers different in the position of substituents and the configuration. For example, explaining 3,8-, 3,9-, 4,8- or 4,9-bis[(diphenylphosphoroxy)methyl]tricyclo[5.2.1.0$^{2,6}$]decane for example, the isomers include (4R,8S)-bis(diphenyl phosphoroxymethyl)-(1R,2S,6R,7R)-tricyclo[5.2.1.0$^{2,6}$]decane, (3R,8R)-bis(diphenylphosphoroxymethyl)-(1R,2S,6S,7R)-tricyclo[5.2.1.0$^{2,6}$]decane, (3S,9R)-bis(diphenylphosphoroxymethyl)-(1S,2R,6R,7S)-tricyclo[5.2.1.0$^{2,6}$]decane, (3S,9S)-bis(diphenylphosphoroxymethyl)-(1S,2R,6R,7S)-tricyclo[5.2.1.0$^{2,6}$]decane, (3S,9R)-bis(diphenylphosphoroxymethyl)-(1R,2R,6R,7S)-tricyclo[5.2.1.0$^{2,6}$]decane, (4S,8S)-bis(diphenyl phosphoroxymethyl)-(1S,2S,6S,7R)-tricyclo[5.2.1.0$^{2,6}$]decane, etc.

The phosphorus-containing compound of the present invention may be a sole compound or a mixture of structural isomers, and may include the above mentioned stereoisomer.

Among the compound represented by the formula (Ic), as the preferred compound, there is exemplified 3,8-, 3,9-, 4,8- or 4,9-bis[(diphenylphosphoroxy)methyl]tricyclo[5.2.1.0$^{2,6}$]decane. Moreover, as the stereoisomer of these compounds, there is exemplified (4R,8S)-bis(diphenylphosphoroxymethyl)-(1R,2S,6R,7R)-tricyclo[5.2.1.0$^{2,6}$]decane.

(iv) Compounds represented by the formula (Id):

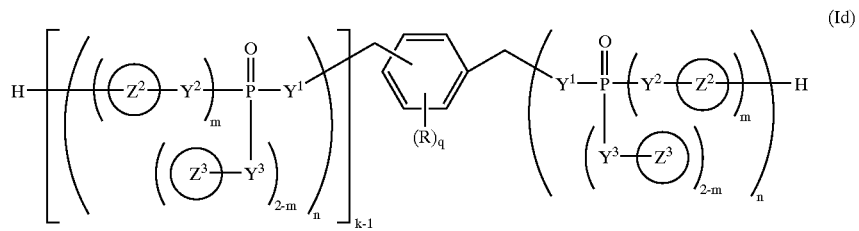

(Id)

wherein $Z^2$, $Z^3$, $Y^1$, $Y^2$, $Y^3$, k, m, n and q have the same meanings as defined above.

In the formula (Id), the preferred ring $Z^2$ and $Z^3$ are benzene rings, and the preferred groups $Y^1$, $Y^2$ and $Y^3$ are —O—.

Among the compounds represented by the formula (Id), as typical compounds, there are exemplified the following compounds.

A phosphorus-containing compound in which the ring $Z^2$ and $Z^3$ are phenyl groups, the groups $Y^1$, $Y^2$ and $Y^3$ are —O—, and m is 1 [e.g., xylyleneglycolbis(diphenyl phosphate) such as o-, m- or p-xylyleneglycolbis(diphenyl phosphate)].

A phosphorus-containing compound in which the ring $Z^2$ and $Z^3$ each is a benzene ring having a substituent ($C_{1-4}$alkyl group), the groups $Y^1$, $Y^2$ and $Y^3$ are —O— and m is 1 [e.g., xylyleneglycolbis(dicresylphosphate) such as o-, m- or p-xylyleneglycolbis(dicresylphosphate), xylyleneglycolbis(dimethylphenylphosphate) such as o-, m- or p-xylyleneglycolbis(2,4-dimethylphenylphosphate), o-, m- or p-xylyleneglycolbis(2,6-dimethylphenylphosphate), and o-, m- or p-xylyleneglycolbis(3,5-dimethylphenyl phosphate)].

Particularly, xylyleneglycolbis(diphenyl phosphate) is preferred.

(v) Compounds represented by the formula (Ie) or (IIa):

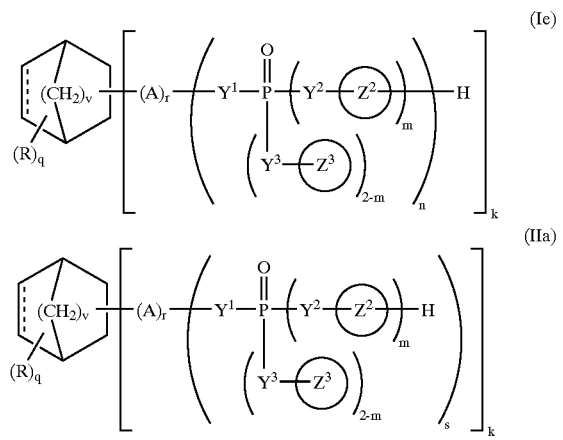

wherein the following structure

=====
----- represents single bond or double bond; v represents an integer of 0 to 2; and the $Z^2$, $Z^3$, R, $Y^1$, $Y^2$, $Y^3$, m, n, k, q, r and s have the same meanings as defined above.

In the formulae (Ie) and (IIa), the preferred rings $Z^2$ and $Z^3$ are benzene rings, and the preferred R is halogen atom, hydroxyl group, $C_{1-6}$alkyl group which may have a substituent, and $C_{1-6}$alkoxy group. Moreover, the preferred groups $Y^1$, $Y^3$ and $Y^3$ are —O—.

Among compounds represented by the formula (Ie), as typical compounds, there are exemplified phosphorus-containing compounds in which the ring $Z^2$ and $Z^3$ each is a benzene ring which may have a substituent (e.g., $C_{1-4}$alkyl group, hydroxyl group), and the groups $Y^1$, $Y^2$ and $Y^3$ are —O— [e.g., bis, tris or tetrakis-(diphenyl phosphoroxy) norbornanes such as 2,3-bis(diphenyl phosphoroxy) norbornane and 2,3,5,6-tetrakis(diphenyl phosphoroxy) norbornane; bis, tris or tetrakis-(diphenyl phosphoroxy$C_{1-4}$alkyl)norbornanes such as 2,5-bis (diphenylphosphoroxymethyl)norbornane and 2,3,5,6-tetrakis(diphenylphosphoroxymethyl)norbornane; bis (diphenylphosphoroxy)$C_{2-4}$alkenylcyclohexanes such as 1,2-bis(diphenylphosphoroxy)-4-vinylcyclohexane; (diphenylphosphoroxy$C_{1-4}$alkyl)cyclohexenes such as 1-diphenylphosphoroxymethyl-3-cyclohexene; mono, di or tri-$C_{1-4}$alkyl(diphenylphosphoroxy$C_{1-4}$alkyl)cyclohexyl phosphates such as 3,3-dimethyl-5-(diphenylphosphoroxy methyl)cyclohexylphosphate].

Moreover, among the compounds represented by the formula (IIa), as typical compounds, there is exemplified a phosphorus-containing compounds in which the ring $Z^2$ and $Z^3$ each is a benzene ring which may have a substituent (e.g., $C_{1-4}$alkyl group, hydroxyl group), $Y^1$, $Y^2$ and $Y^3$ are —O—, k is 2 to 6, at least one of s is 2 to 4, and A corresponding to the factor (coefficient) s is $C_{1-4}$alkylene group [e.g., bis(diphenylphosphoroxy)-[bis(diphenyl phosphoroxy)$C_{1-4}$alkyl]cyclohexane such as 1,2-bis(diphenylphosphoroxy)-4-[1',2'-bis(diphenyl phosphoroxy)ethyl]cyclohexane].

As the preferred compound, there are exemplified 2,5-bis (diphenylphosphoroxymethyl)norbornane, 2,3-bis (diphenylphosphoroxy)norbornane, 1,2-bis(diphenyl phosphoroxy)-4-vinylcyclohexane, 3,3-dimethyl-5-(diphenylphosphoroxymethyl)cyclohexylphosphate, 1,2-bis (diphenylphosphoroxy)-4-[1',2'-bis(diphenyl phosphoroxy) ethyl]cyclohexane, and 1-diphenylphosphoroxy methyl-3-cyclohexene.

(23/21)
(vi) Compounds represented by the formula (If):

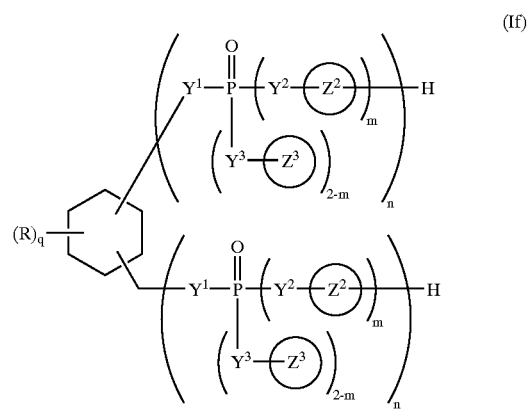

wherein R, $Y^1$, $Y^2$, $Y^3$, $Z^2$, $Z^3$, m, n and q have the same meanings as defined above.

The formula (If) corresponds to a phosphorus-containing compound wherein k is 2, one of r is 1, and v is 0 in the formula (Ie).

In the formula (If), the preferred rings $Z^2$ and $Z^3$ each is a benzene ring, and the preferred R is halogen atom, hydroxyl group, $C_{1-6}$alkyl group or $C_{1-6}$alkoxy group. Moreover, the preferred groups $Y^1$, $Y^2$ and $Y^3$ each is a —O— or —$NR^1$—.

Among compounds represented by the formula (If), as typical compounds, there are exemplified the following compounds.

A phosphorus-containing compounds in which the rings $Z^2$ and $Z^3$ each is a benzene ring which may have a substituent (e.g., $C_{1-4}$alkyl group, hydroxyl group), and the groups $Y^1$, $Y^2$ and $Y^3$ are —O— [e.g., 1-diphenylphosphoroxy-3-diphenylphosphoroxymethyl cyclohexane, 3,3-dimethyl-5-(diphenylphosphoroxymethyl) cyclohexylphosphate].

A phosphorus-containing compounds in which the ring $Z^2$ and $Z^3$ each is a benzene ring which may have a substituent (e.g., $C_{1-4}$alkyl group, hydroxyl group), and the groups $Y^1$, $Y^2$ and $Y^3$ are —$NR^1$— [e.g., 1-diphenyl phosphorylamino-3-diphenylphosphorylaminomethyl cyclohexane, 3,3-dimethyl-5-(diphenylphosphorylamino methyl) cyclohexylphosphoramide].

(vii) Compounds represented by the formula (IIIa):

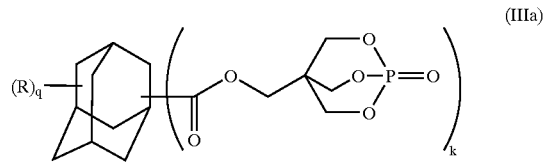

wherein R, q and k have the same meanings as defined above.

In the formula (IIIa), the preferred R is hydrogen atom, carboxyl group, halocarboxyl group, or $C_{1-4}$alkyl group.

Among the compounds represented by the formula (IIIa), as typical compounds, there are exemplified a phosphorus-containing compounds in which R is $C_{1-4}$alkyl group, and k is 1 to 4 [e.g., (1-oxo-2,6,7-trioxa-1-phosphabicyclo[2.2.2]-oct-4-yl)methyl adamantane carbonate, bis(1-oxo-2,6,7-trioxa-1-phosphabicyclo [2.2.2]-oct-4-yl)methyl adamantanedicarbonate, (1-oxo-2,6,7-trioxa-1- phosphabicyclo[2.2.2]-oct-4-yl)methyl dimethyl-adamantanecarbonate, bis(1-oxo-2,6,7-trioxa-1-phosphabicyclo[2.2.2]-oct-4-yl)methyl dimethyl-adamantanedicarbonate, tris(1-oxo-2,6,7-trioxa-1-phosphabicyclo[2.2.2]-oct-4-yl)methyl adamantanetricarbonate, and tetrakis(1-oxo-2,6,7-trioxa-1-phosphabicyclo[2.2.2]-oct-4-yl)methyl adamantanetetracarbonate].

[Production Process]

The phosphorus-containing compound (I), (II) or (III) of the present invention can be prepared by reacting a compound represented by the following formula (I-1), (II-1) or (III-1) and a phosphorus compound represented by the following formula (I-2), (II-2) or (III-3).

Such process gives a high-purity phosphorus-containing compound with high yield by simple manner.

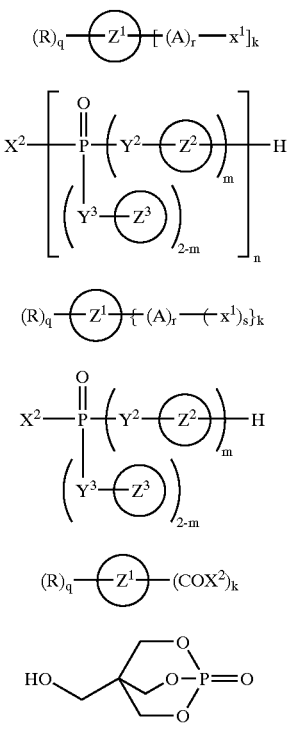

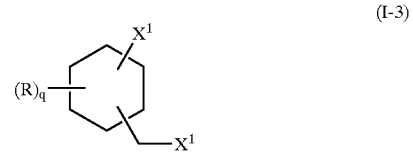

wherein $X^1$ represents hydroxyl group, thiol group, amino group or substituted amino group; $X^2$ represents halogen atom, hydroxyl group, or alkoxy group; $Z^1$, $Z^2$, $Z^3$, R $Y^1$, $Y^2$, $Y^3$, k, m, q, r and s have the same meanings as defined above.

As the substituted amino group represented by $X^1$, there are exemplified alkyl-substituted amino groups (e.g., mono or di$C_{1-4}$alkylamino groups such as methylamino, ethylamino, dimethylamino, diethylamino, and methylethylamino groups).

As the halogen atom represented by $X^2$, there are exemplified fluorine, chlorine, bromine, and iodine atoms (particularly chlorine atom). As the alkoxy group, there are exemplified the above exemplified $C_{1-8}$alkoxy groups (particularly $C_{1-4}$alkoxy groups such as methoxy and ethoxy groups) and $C_{6-10}$aryloxy groups such as phenyloxy group.

Moreover, the compound represented by the formula (I-1) mentioned above includes a compound represented by the following formula (I-3):

wherein R, $X^1$ and q have the same meanings as defined above.

More concretely, as the compound represented by the formula (I-1), the following compounds are exemplified.

(1) A compound in which the $X^1$ is hydroxyl group, for example, a compound in which the ring $Z^1$ is adamantane ring which may have a substituent (e.g., alkyl group, alkoxy group) [adamantanemonools which may have a substituent such as adamantanol, dimethyladamantanol, diethyladamantanol, and dimethoxyadamantanol; adamantanediols which may have a substituent such as adamantanediol, dimethyladamantanediol, and diethyladamantanediol; adamantanetriol, adamantanetetraol];

a compound in which the ring $Z^1$ is tricyclo[5.2.1.0$^{2,6}$] decane ring [1(R),2(S),6(S),7(R)-[5.2.1.0$^{2,6}$]tricyclodecane-3(R),8(R)-dimethanol, 1(S),2(R),6(R),7(S)-[5.2.1.0$^{2,6}$]tricyclodecane-3(S),9(R)-dimethanol, 1(S),2(R),6(R),7(S)-[5.2.1.0$^{2,6}$]tricyclodecane-3(S),9(S)-dimethanol, 1(R),2(R),6(R),7(S)-[5.2.1.0$^{2,6}$]tricyclodecane-3(S),9(R)-dimethanol, 1(S),2(S),6(S),7(R)-[5.2.1.0$^{2,6}$]tricyclodecane-4(S),8(S)-dimethanol];

a compound in which the ring $Z^1$ is benzene ring (e.g., o-xylyleneglycol, m-xylyleneglycol, p-xylyleneglycol);

a compound in which the ring $Z^1$ is cyclohexane ring or norbornane ring having a substituent [e.g., 4-vinylcyclohexane-1,2-diol, 4-(1,2'-dihydroxyethyl) cyclohexane-1,2-diol, norbornanedimethanol, norbornane-2,5-diol, 3-cyclohexenemethanol, 3-hydroxymethyl-5,5-dimethylcyclohexanol].

(2) A compound in which $X^1$ is thiol group, for example, a compound having adamantane ring which may have a substituent as the ring $Z^1$ (e.g., adamantanethiol).

(3) A compound in which the $X^1$ is amino group or N-substituted amino group, for example, a compound having adamantane ring which may have a substituent as the ring $Z^1$ [e.g., aminoadamantane, N-$C_{1-4}$alkylaminoadamantane(N-methylaminoadamantane), dimethyladamantaneamine, diaminoadamantane, dimethyladamantanediamine, triaminoadamantane, tetraaminoadamantane].

Among the compounds represented by the formula (I-1), (i) a useful compound for preparing the compound of the formula (Ia) includes adamantanediol, dimethyladamantanediol, and adamantanetriol.

(ii) As a useful compound for preparing the compound of the formula (Ib), there are exemplified adamantanol, dimethyladamantanol, adamantanediol, dimethyladamantanediol, adamantanetriol, and adamantaneamine.

(iii) As a useful compound for preparing the compound of the formula (Ic), there are exemplified 1(R),2(S),6(S),7(R)-[5.2.1.0$^{2,6}$]tricyclodecane-3(R),8(R)-dimethanol, 1(S),2(R), 6(R),7(S)-[5.2.1.0$^{2,6}$]tricyclodecane-3(S),9(R)-dimethanol, 1(S),2(R),6(R),7(S)-[5.2.1.0$^{2,6}$]tricyclodecane-3(S),9(S)-dimethanol, 1(R),2(R),6(R),7(S)-[5.2.1.0$^{2,6}$]tricyclodecane-3(S),9(R)-dimethanol, and 1(S),2(S),6(S),7(R)-[5.2.1.0$^{2,6}$]tricyclodecane-4(S),8(S)-dimethanol. When these compounds are used as raw materials, these compounds may be a mixture of structural isomers, and may be a sole compound. Moreover, these compounds may include a stereoisomer of the compound.

(iv) A useful compound for preparing the compound of the formula (Id) includes xylyleneglycols (o-, m- or p-xylyleneglycol).

(v) As a useful compound for preparing the compound of the formula (Ie), there may be exemplified norbornanedimethanol, 2,3-dihydroxynorbornane, 1,2-dihydroxy-4-vinylcyclohexane, 1,2-dihydroxy-4-(1',2'-dihydroxyethyl)cyclohexane, 3-cyclohexen-1-methanol, and 3-hydroxymethyl-5,5-dimethylcyclohexanol.

(vi) A compound useful for preparing the compound of the formula (If) includes the compounds represented by the formula (I-3) [e.g., 3-hydroxymethylcyclohexanol, 3-hydroxymethyl-5,5-dimethylcyclohexanol, 3-aminomethylcyclohexaneamine, and 3-aminomethyl-5,5-dimethylcyclohexaneamine].

As a compound represented by the formula (I-2), the following compounds may be exemplified.

A compound in which the $X^2$ is halogen atom [e.g., $diC_{6-10}$arylphosphoric halides such as diphenylphosphoric chloride, ditoluylphosphoric chloride, dixylylphosphoric chloride, and dicresylphosphoric chloride; bis(tricyclo$C_{8-12}$alkyloxy)phosphoric halides such as bis(adamantyloxy)phosphoric chloride; tricyclo$C_{8-12}$alkyloxy$C_{6-10}$arylphosphoric halides such as adamantyloxyphenylphosphoric chloride].

A compound in which the $X^2$ is hydroxyl group [e.g., $diC_{6-10}$arylphosphates such as diphenylphosphoric ester (diphenylphosphate), ditoluylphosphoric ester (ditoluylphosphate), dixylylphosphoric ester (dixylylphosphate), and dicresylphosphoric ester (dicresylphosphate); tricyclo$C_{8-12}$alkyl-$C_{6-10}$arylphosphates such as adamantylphenylphosphoric ester; bis(tricyclo$C_{8-12}$alkyl)phosphates such as bisadamantylphosphoric ester].

A compound in which the $X^2$ is alkoxy group [e.g., tri$C_{6-10}$arylphosphates such as triphenylphosphate (TPP) and tricresylphosphate; mono$C_{1-4}$alkyl-di$C_{6-10}$arylphosphates such as methyldiphenylphosphate and ethyldiphenylphosphate; tricyclo$C_{8-12}$alkyl-di$C_{6-10}$arylphosphates such as diphenyladamantylphosphate].

Incidentally, as the compounds of the formula (I-2), commercially available products may be used, and may be prepared by reacting a phosphorus compound having 1 to 3 of the group $X^2$ (e.g., phosphorus oxychloride, phenylphosphoric dichloride, phenylphosphoric acid) with alcohols having the ring $Z^2$ and/or $Z^3$ (e.g., adamantanol), thiols (adamantane thiol), or amines (aminoadamantane).

Among the compounds of the formula (I-2), as a useful compound for preparing (i) the compound of the formula (Ia), (ii) the compound of the formula (Ib), (iii) the compound of the formula (Ic), (vi) the compound of the formula (Id), or (v) the compound of the formula (Ie), there may be exemplified di$C_{6-12}$arylphosphoric chlorides such as diphenylphosphoric chloride; di$C_{6-12}$arylphosphates such as diphenylphosphoric acid; and TPP. Moreover, phosphorus oxychloride, phenylphosphoric dichloride, phenylphosphoric acid, etc may be used.

The compound represented by the formula (II-1) includes, for example, a compound in which $X^1$ is hydroxyl group [e.g., (mono or di-hydroxy$C_{1-4}$alkyl)$C_{4-10}$cycloalkanes such as (1,2-dihydroxyethyl)cyclohexane and 1,2-dihydroxy-4-(1,2-dihydroxyethyl)cyclohexane].

The compound represented by the formula (II-2) corresponds to a compound in which n is 1 in the formula (I-2).

The compound represented by the formula (III-1) includes, for example, the following compounds.

A compound having halogen atom as $X^2$ and adamantane ring as the ring $Z^1$, for example, a compound in which k is 1 [e.g., adamantanecarboxylic chloride, dimethyl adamantanecarboxylic chloride, diethyladamantane carboxylic chloride, adamantanecarboxylic bromide, dimethyladamantanecarboxylic bromide, diethyladamantane carboxylic bromide]; a compound in which k is 2 [e.g., adamantanedicarboxylic dichloride, dimethyladamantane dicarboxylic dichloride, diethyladamantanedicarboxylic dichloride, adamantanedicarboxylic dibromide, dimethyl adamantanedicarboxylic dibromide, diethyladamantane dicarboxylic dibromide]; a compound in which k is 3 [ e.g., adamantanetricarboxylic trichloride, adamantane tricarboxylic tribromide]; a compound in which k is 4 [e.g., adamantanetetracarboxylic tetrachloride, adamantane tetracarboxylic tetrabromide].

A compound having hydroxyl group as $X^2$ and adamantane ring as the ring $Z^1$, for example, a compound in which k is 1 [e.g., adamantanecarboxylic acid, dimethyladamantane carboxylic acid, diethyladamantanecarboxylic acid]; a compound in which k is 2 [e. g., adamantanedicarboxylic acid, dimethyladamantanedicarboxylic acid, diethyladamantane dicarboxylic acid]; a compound in which k is 3 [e.g., adamantanetricarboxylic acid]; a compound in which k is 4 [e.g., adamantanetetracarboxylic acid].

Among the compounds represented by the formula (III-1), as a useful compound for preparing (vii) the compound of the formula (IIIa), there are exemplified adamantanecarboxylic chloride, adamantanecarboxylic acid, adamantanedicarboxylic chloride, adamantanedicarboxylic dichloride.

The amount of the phosphorus compound of the formula (I-2) or (II-2) can be selected within the wide range according to the object compound, relative to 1 mol of the $X^1$ group of the compound of the formula (I-1) (or the formula (I-3)) or (II-2), for example, within the range of about 0.1 to 50 mol, preferably about 0.3 to 30 mol, and more preferably about 0.5 to 10 mol.

More concretely, (i) in the case where the phosphorus-containing compound of the formula (Ia) is prepared, the amount of the phosphorus compound (I-2) is, for example, about 0.1 to 50 mol relative to 1 mol of the compound (I-1) having one $X^1$ group, and is about 0.5 to 100 mol relative to 1 mol of the compound (I-1) having two $X^1$ groups. Further, the amount of the phosphorus compound of the formula (I-2) is about 0.5 to 150 mol relative to 1 mol of the compound (I-1) having three $X^1$ groups, and is about 0.5 to 200 mol relative to 1 mol of the compound (I-1) having four $X^1$ groups.

(ii) In the production of the phosphorus-containing compound of the formula (Ib), the amount of the phosphorus compound (I-2) is, for example, about 0.1 to 20 mol, preferably about 0.2 to 10 mol, more preferably about 1.5 to 5.0 mol, and particularly about 1.5 to 2.5 mol, relative to 1 mol of the compound (I-1) having one $X^1$ group.

(iii) In the production of the phosphorus-containing compound of the formula (Ic), the amount of the phosphorus compound (I-2) is, for example, about 0.1 to 20 mol, preferably about 0.2 to 10 mol, about 1.0 to 10 mol, and particularly about 1.5 to 5.0 mol. relative to 1 mol of the compound (I-1) having two $X^1$ groups.

(iv) In the case where the phosphorus-containing compound of the formula (Id) is prepared, the amount of the phosphorus compound (I-2) is, for example, about 0.1 to 5 mol, preferably about 0.2 to 3 mol, more preferably about 0.5 to 2 mol, particularly about 1 to 2 mol, relative to 1 mol of the compound (I-1) having two $X^1$ groups.

(v) In the production of the phosphorus-containing compound of the formula (Ie) or (IIa), the amount of the phosphorus compound (I-2) is, for example, about 0.1 to 50 mol relative to 1 mol of the compound (I-1) having one $X^1$ group, about 0.5 to 150 mol equivalent relative to 1 mol of the compound (I-1) having two $X^1$ groups, and further is about 0.5 to 200 mol equivalent, relative to 1 mol of the compound (I-1) having four $X^1$ groups.

(vi) In the case where the phosphorus-containing compound of the formula (If) is prepared, the amount of the phosphorus compound (I-2) is, for example, about 0.5 to 100 mol, relative to 1 mol of the compound (I-3).

The amount of the compound of the formula (III-1) can be selected within the wide range according to the object compound, and is, for example, about 0.1 to 50 mol, preferably about 0.3 to 30 mol, and more preferably about 0.5 to 10 mol, relative to 1 mol of the compound of the formula (III-2).

More concretely, (vii) in the production of the phosphorus-containing compound of the formula (IIIa), the amount of the compound of the formula (III-1) having one $X^2$ group is, relative to 1 mol of the phosphorus compound of the formula (III-2), about 1.0 to 5.0 mol, preferably about 1.0 to 2.5 mol. Moreover, the amount of the compound of the formula (II-1) having two $X^2$ groups is about 0.1 to 10 mol, preferably about 0.1 to 5.0 mol.

Incidentally, when a polyvalent phosphorus compound (e.g., phenylphosphoric dichloride) is used as a raw material for the compound (I-2) or (I-3), the amount of the polyvalent phosphorus compound is about 0.2 to 10 mol (e.g., 0.2 to 0.5 mol), preferably about 0.25 to 5 mol (e.g., 0.25 to 0.45 mol), and more preferably about 0.3 to 1 mol, relative to 1 mol of the compound of the formula (I-1).

The reaction described above may be conducted in the absence of a solvent, and is usually effected in the presence of a solvent. The species of the solvent is not particularly restricted to a specific solvent so far as the reaction is not inhibited, and is exemplified a nitrogen-containing hydrocarbon which may show a basic (e.g., heterocyclic compounds such as pyridine and picoline; nitrile-series solvents such as acetonitrile and benzonitrile); aliphatic hydrocarbons (e.g., hexane, heptane, octane); aromatic hydrocarbons (e.g., benzene, toluene, xylene, ethylbenzene); oxygen-containing hydrocarbons (e.g., ketones such as acetone and methylethylketone; ethers such as diethylether, dibutylether, tetrahydrofuran, and 1,4-dioxane; esters such as ethyl acetate); halogenated hydrocarbons (e.g., carbon tetrachloride, chloroform, dichloromethane, 1,2-dichloroethane, dichlorobenzene). These solvents may be used either a sole solvent or a mixed solvent.

The preferred solvent includes pyridine, nitrile-series solvents such as acetonitrile; $C_{6-8}$aliphatic hydrocarbons such as normal hexane and normal heptane; $C_{6-12}$aromatic hydrocarbons such as toluene and xylene; ethers such as diethylether, tetrahydrofuran, and 1,4-dioxane; halogenated hydrocarbons such as chloroform, dichloromethane, and 1,2-dichloroethane. Further preferably, pyridine, acetonitrile, tetrahydrofuran, 1,2-dichloroethane, dichloromethane and chloroform are used.

The amount of the solvent is not restricted so far as the reaction is not adversely affected, and is, for example, about 0.1 to 500 mol, preferably about 1 to 100 mol, more preferably about 1 to 50 mol, relative to 1 mol of the compound represented by the formula (I-1), (II-1) or (III-1).

The objective phosphorus-containing compound represented by the formula (I) or (II) can be obtained by a dehalogenation reaction when $X^2$ in the compound (I-2) or (II-1) is halogen atom, a dehydration reaction when $X^2$ in the compound (I-2) or (II-1) is hydroxyl group, or a transesterification reaction when $X^2$ in the compound (I-2) or (II-1) is alkoxy group. The reaction described above may be effected in the presence or absence of a catalyst.

Particularly, when the $X^2$ is halogen atom in the compound of the formula (I-2), (II-2) or (III-1), the reaction may be effected in the presence of a dehydrohalogenation reagent. As the dehydrohalogenation reagent, there are exemplified various compounds including the following compound;

(i) amines primary amines [$C_{1-8}$alkylamines (aliphatic primary amines) such as t-butylamine, t-pentylamine, t-hexylamine, and t-octylamine; $C_{3-8}$cyclohexylamines (alicyclic primary amines) such as cyclohexylamine; $C_{6-10}$arylamines (aromatic primary amines) such as aniline], secondary amines [di$C_{1-8}$alkylamines (aliphatic secondary amines) such as di-t-butylamine, di-t-pentylamine, di-t-hexylamine, and di-t-octylamine; di$C_{3-8}$cyclohexylamines (alicyclic secondary amines) such as dicyclohexylamine; $C_{1-4}$alkylanilines (aromatic secondary amines) such as N-methylaniline], tertiary amines [tri$C_{3-8}$alkylamines (aliphatic tertiary amines) such as trimethylamine and triethylamine; tri$C_{3-8}$cyclohexylamines (alicyclic tertiary amines) such as tricyclohexylamine; N,N-di$C_{1-4}$alkylanilines (aromatic tertiary amines) such as N,N-diethylaniline];

(ii) aromatic cyclic bases for example, 5-membered cyclic compounds (heterocyclic compounds having one to three nitrogen(s) such as pyrrole, 3-pyrroline, pyrazole, 2-pyrazoline, imidazole, 1,2,3-triazole, and 1,2,4-triazole), 6-membered cyclic compounds (heterocyclic compounds having one to three nitrogen(s) such as pyridine; N-substituted pyridines such as 4-dimethylaminopyridine, 2-piperidinopyridine, 3-piperidinopyridine, 4-piperidinopyridine, 2-pyriridinopyridine, 3-pyriridinopyridine, and 4-pyriridinopyridine; pyridazine; pyrimidine; pyrazine; N-subsituted pyrazine such as 2-methylpyrazine; s-triazine; picoline), polycyclic heterocyclic compounds (condensed heterocyclic compounds of an aromatic hydrocarbon ring and a heterocycle such as indole, quinoline, isoquinoline, cinnoline, quinoxaline, quinazoline, phthalazine, and 1,10-phenanthroline; and assembled heterocyclic compounds such as 2,2-bipyridyl ring);

(iii) aliphatic cyclic bases for example, 5-membered cyclic compounds (e.g., pyrrolidine; N-substituted pyrrolidines such as N-methylpyrrolidine, 2-methylpyrrolidine, 3-methylpyrrolidine, 2-aminopyrrolidine, and 3-aminopyrrolidine; pyrazolidine), 6-membered cyclic compounds (piperidine; N-substituted piperidines such as N-methylpiperidine, o-aminopiperidine, m-aminopiperidine, and p-aminopiperidine; piperylhydradine; morpholine; piperazine; N-substituted piperazines such as N-methylpiperazine, 2-methylpiperazine, and N,N-dimethylpiperazine); polycyclic heterocyclic compounds (crosslinked cyclic compounds such as quinuclidine, 1,4-diazabicyclo[2.2.2]octane, 1,5-diazabicyclo[3.2.1]octane, 1,5-diazabicyclo[3.3.0]octane, 1,4-diazabicyclo[4.2.0] octane, 1,5-diazabicyclo[3.3.1]nonane, 1,5-diaza bicyclo [5.3.0]decane, 1,5-diazabicyclo[3.3.0.0$^{2,6}$]octane, 1,8-diazabicyclo[5.4.0]undeca-7-ene, 1,5-diaza bicyclo[4.3.0] nona-5-ene, and hexamethylenetetramine);

(iv) amides (e.g., N,N-di$C_{1-4}$alkyl substituted amides such as N,N-dimethylformamide and N,N-dimethylacetamide);

(v) hydroxides of alkaline metal or alkaline earth metal (e.g., sodium hydroxide, calcium hydroxide).

The preferred catalyst includes the tertiary amines (tri-$C_{1-4}$alkylamines such as triethylamine), the aromatic cyclic bases (preferably 6-membered heterocyclic compounds such as pyridine and picoline), the aliphatic cyclic bases (e.g., 6-membered heterocyclic compounds such as piperazine and N-methylpiperazine, quinuclidine, 1,4-diazabicyclo [2.2.2]octane, and hexamethylene tetramine), the amides (e.g., N,N-dimethylformamide), the metal hydroxide (e.g., sodium hydroxide). Particularly the preferred catalysts are pyridine etc.

The amount of the dehydrohalogenation reagent can be selected within the range of about 0.5 to 50 mol, and preferably about 1 to 30 mol, relative to 1 mol of the compound of the formula (I-2), (II-2) or (III-1).

More concretely, (i) when the phosphorus-containing compound of the formula (Ia) is prepared, the amount of the dehydrohalogenation reagent is about 0.5 to 30 mol, and preferably about 1.0 to 15 mol, relative to 1 mol of the compound of the formula (I-2) or (II-2).

(ii) When the phosphorus-containing compound of the formula (Ib) is produced, the amount of the dehydrohalogenation reagent is about 0.5 to 30 mol, and preferably about 1.0 to 15 mol, relative to 1 mol of the compound of the formula (I-2).

(iii) In the production of the phosphorus-containing compound of the formula (Ic), the amount of the dehydrohalogenation reagent is about 0.5 to 30 mol, and preferably about 1.0 to 15 mol, relative to 1 mol of the compound of the formula (I-2).

(iv) When the phosphorus-containing compound of the formula (Id) is prepared, the amount of the dehydrohalogenation reagent is about 0.5 to 30 mol, and preferably about 1.0 to 15 mol, relative to 1 mol of the compound of the formula (I-2).

(v) In the production of the phosphorus-containing compound of the formula (Ie) or (IIa), the amount of the dehydrohalogenation reagent is about 0.5 to 5.0 mol, and preferably about 0.7 to 2.5 mol, relative to 1 mol of the compound of the formula (I-2) or (II-2).

(vi) When the phosphorus-containing compound of the formula (If) is prepared, the amount of the dehydrohalogenation reagent is about 0.5 to 30 mol, and preferably about 1.0 to 15 mol, relative to 1 mol of the compound of the formula (I-2).

(vii) The phosphorus-containing compound of the formula (IIa) is prepared by using the dehydrohalogenation reagent in an amount of about 2 to 10 mol, and preferably about 2.5 to 7 mol, relative to 1 mol of the compound of the formula (II-1).

Incidentally, the dehydrohalogenation reagent (e.g., pyridine) may be used as a solvent.

Moreover, in the compound of the formula (I-2), (II-2) or (III-1), when $X^2$ is hydroxyl group and/or alkoxy group, a conventional catalyst (acid catalyst, basic catalyst) may be used in the reaction (dehydration and/or transesterification). As the acid catalyst, there may be exemplified a Lewis acid such as aluminium chloride, magnesium chloride, titanium tetrachloride, antimony pentachloride, zinc chloride, and tin chloride; and a mineral acid such as sulfuric acid and hydrochloric acid. Moreover, as the basic catalyst, there are exemplified amines ($C_{1-8}$alkylamines such as t-butylamine, t-pentylamine, t-hexylamine, and t-octylamine: $diC_{1-8}$alkylamines such as di-t-butylamine, di-t-pentylamine, di-t-hexylamine, and di-t-octylamine; $triC_{1-8}$alkylamines such as trimethylamine, triethylamine, and tributylamine), and hydroxides of alkaline metal or alkaline earth metal (e.g., sodium hydroxide, calcium hydroxide).

Incidentally, the order of the addition of each component is not restricted, for example, when the dehydrohalogenation is effected (the case in which $X^2$ is halogen atom), at first the compound of the formula (I-1) (including the formula (I-3)), (II-1) or (II-2) may be dissolved in the solvent mentioned above, and the compound of the formula (I-2), (II-2) or (III-1) may be added to the reaction system to react each other. Moreover, when the dehydrohalogenation reagent is used, the dehydrohalogenation reagent may be dissolved in the solvent together with the compound of the formula (I-1). (II-1) or (III-2), and may be added by dropping etc with or after adding the compound of the formula (I-2), (II-2) or (III-1).

Moreover, when the dehydration or transesterification is effected, for example, the compound of the formula (I-1), (II-1) or (III-2) and the compound of the formula (I-2), (II-2) or (II-1) may be reacted in the solvent mentioned above.

The reaction temperature may be selected within the range of about −80° C. to 250° C. (e.g., about −10° C. to 250° C.), and is, for example, about −80° C. to 200° C., preferably about −50° C. to 180° C., more preferably about −20° C. to 150° C., and particularly about 0° C. to 150° C. (e.g., about 10° C. to 120° C.). Incidentally, when the compound represented by the formula (Ie) is prepared, too high reaction temperature is not preferred since the object compound is liable to decompose. Therefore, the reaction temperature can be selected within the range of about −80° C. to 100° C., and is preferable, for example, about −50° C. to 50° C., and preferably −20° C. to 30° C.

The reaction may be conducted under ordinary pressure, reduced pressure, or applied pressure. The reaction may be carried out in an atmosphere of an inert gas (e.g., nitrogen, argon, helium).

After the completion of the reaction, the phosphorus-containing compound (I), (II) and (III) formed in the above-described reaction can easily be separated and purified by such a conventional means as filtration, condensation, distillation, extraction, crystallization, recrystallization, column chromatography, or a combination means thereof.

Since the phosphorus-containing compound of the present invention is excellent in heat resistance and stability, the phosphorus-containing compound is useful as additives (flame retardants, stabilizer such as antioxidant) to improve the properties of various materials [e.g., materials required heat resistance and stability such as adhesives (e.g., hot-melt adhesives, thermosensitive tackifiers, delayed tack adhesives), materials for photography and printing (e.g., image-receiving materials for forming an image by thermal transfer, photosensitizer for color photography, meltable inks for ink jet), shock-absorbing materials, and pencil lead], and organic compounds or a mixture thereof (e.g., organic polymer compounds such as lubricants and heat transfer mediums). Further, the phosphorus-containing compound is useful as plasticizers for resins. Moreover, since the phosphorus-containing compound of the present invention not only imparts high flame retardancy to resins but also has a low volatility, the phosphorus-containing compound is excellent in handling and useful as stabilizer such as flame retardant.

The characteristics or properties of resins and a flame-retardancy level can be improved by addition of the phosphorus-containing compound of the present invention to various resins, particularly resins for molding. The resin includes, for example, thermoplastic resins [e.g., olefinic resins (e.g., polypropylene-series resins, polyethylene-series resins), halogen-containing resins (e.g., vinyl chloride), acrylic resins [e.g., poly(meth)acrylates such as polymethyl methacrylate], styrenic resins [e.g., polystyrene, rubber-grafted styrenic resins or rubber-reinforced styrenic resins (e.g., HIPS, acrylonitrile-rubber component(e.g., butadiene)-styrene copolymers (e.g., ABS resins), acrylonitrile-styrene copolymers (SAN resins)], polycarbonate-series resins, polyester-series resins (e.g., polyalkylene arylates such as polyethylene terephthalate and polybutylene terephthalate), polyethylene ether-series resin, polyphenylene sulfide-series resins, polyamide-series resins (e.g., aliphatic polyamides such as nylon 6 and nylon 12, aromatic nylons), polyurethane resins, polyether-series resins (e.g., polyacetal resins, polyarylate resins, denatured polyphenylene resins (e.g., PPO)], thermosetting resins (e.g., alkyd resins, allyl resins, epoxy resins, hard urethane resins, soft urethane resins, phenolic resins, melamine resins, guanamine resins, xylene resins, acrylic resins, unsaturated polyester resins, silicone resins, urea resins, butadiene-series resins, polyimide resins).

Moreover, the resins may be copolymer resins [e.g., methyl methacrylate-butadiene-styrene copolymers (MBS resins), styrene-maleic anhydride copolymers, styrene-methacrylic acid copolymers] and alloys (e.g., an alloy of ABS resin or HIPS resin and polycarbonate-series resin, an alloy of ABS resin and polyester-series resin, an alloy of ABS resin and polyamide-series resin).

Among the thermoplastic resins or the thermosetting resins, the styrenic resins may be a homopolymer or a copolymer of styrene and styrene derivatives such as α-substituted or nucleus (aromatic ring)-substituted styrene. Moreover, the styrenic resins also include a copolymer, in which a predominant component is the above mentioned monomer, and other component is a vinyl compound (e.g., acrylonitrile, acrylic acid, methacrylic acid) and/or a conjugated diene compound (e.g., butadiene, isoprene). As such styrenic resins, there are exemplified polystyrene, high impact polystyrene (HIPS), acrylonitrile-butadiene-styrene copolymer (ABS resin), acrylonitrile-styrene copolymer (AS resin), styrene-methacrylate copolymer (MS resin), styrene-butadiene copolymer (SBS resin).

Moreover, the styrenic resin and other resins (particularly the polycarbonate-series resin) may be used in combination. The ratio of the styrenic resin to the other resin may be the former/the latter (weight ratio)=about 50/50 to 15/85, and preferably about 40/60 to 20/80.

When the phosphorus-containing compound is used as an additive for the resins, the amount of the phosphorus-containing compound is not restricted so far as the properties of the resins are not adversely affected, and is, relative to 100 parts by weight of resins, about 1 to 40 parts by weight, and preferably about 3 to 25 parts by weight.

Incidentally, so far as the properties of the resins are not deteriorated, to the resins, other additives [e.g., lubricants such as stearic acid and ethylenebisstearyl amide, flame retardants (e.g., inorganic phosphorus-series flame retardants such as red phosphorus; triazine-series flame retardants such as melamine cyanulate, melamine, and cyanuric acid; metal hydrates; borates; metal oxides), auxiliary flame retardants (e.g., fluorine resins, silicone), stabilizers (e.g., antioxidants, ultraviolet-rays absorbent), dyes, pigments, fillers (e.g., glass fiber, carbon fiber, wollastonite, calcium carbonate, talc, mica, wood flour, slate powder, fibrous asbestos) may be added in addition to the phosphorus-containing compound of the present invention.

A resin composition comprising the resins and various additives (e.g., phosphorus-containing compound) can be produced by a conventional kneading technique (e.g., the use of kneading machines such as extruder, heat(hot) roll, kneader, and Banbury mixer).

Such resin compositions are excellent in flame retardancy and heat resistance, and thus can be used over wide applications [e.g., parts for a variety of fields (OA equipment fields, fields for electrical household appliances and electrical equipment, electrical and electronics fields, telecommunication equipment fields, sanitation fields, car fields, fields for accommodation unit such as furniture and building materials, general merchandise fields), housing, chassis].

INDUSTRIAL APPLICABILITY

Since the phosphorus-containing compound of the present invention has a specific ring structure, the phosphorus-containing compound is excellent in heat resistance, and a combination of the phosphorus-containing compound with various materials (particularly resins for molding) can markedly improve the properties (e.g., stability) of the composition.

EXAMPLES

The following examples are intended to describe this invention in further detail and should by no means be interpreted as defining the scope of the invention.

Example A1

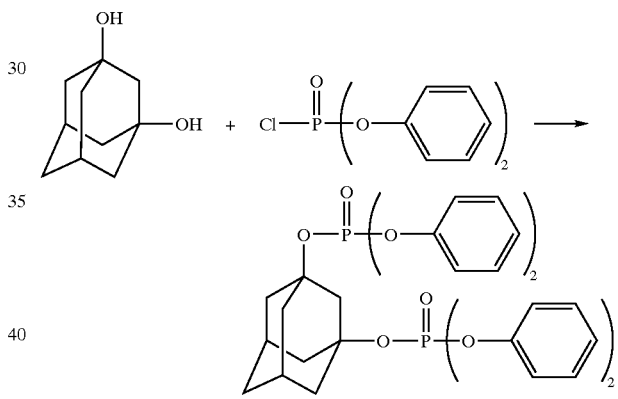

Adamantylbis(diphenylphosphate) was prepared according to the reaction scheme.

Into a three-neck flask (500 ml) equipped with a dropping funnel, a Dimroth condenser and a calcium chroride ($CaCl_2$) tube, were fed 40.1 g (238 mmol) of adamantanediol and 235.1 g (2.97 mol) of pyridine, and 159.7 g (595 mmol) of diphenylphosphorochloridate was added dropwise to the mixture for 30 minutes at 60° C. with stirring. After dropping was completed, the reaction was effected at 90° C. for 2.5 hours.

The reaction mixture was cooled to room temperature, and 400 ml of ethyl acetate and 400 ml of water were added to the reaction mixture for extraction of an object compound. Further, an organic layer was washed with 400 ml of 2N (2 mol/L) hydrochloric acid three times, 400 ml of saturated sodium carbonate aqueous solution three times, and 400 ml of water one time in this order. The organic layer was dried with sodium sulfate and evaporated.

Figure 2:
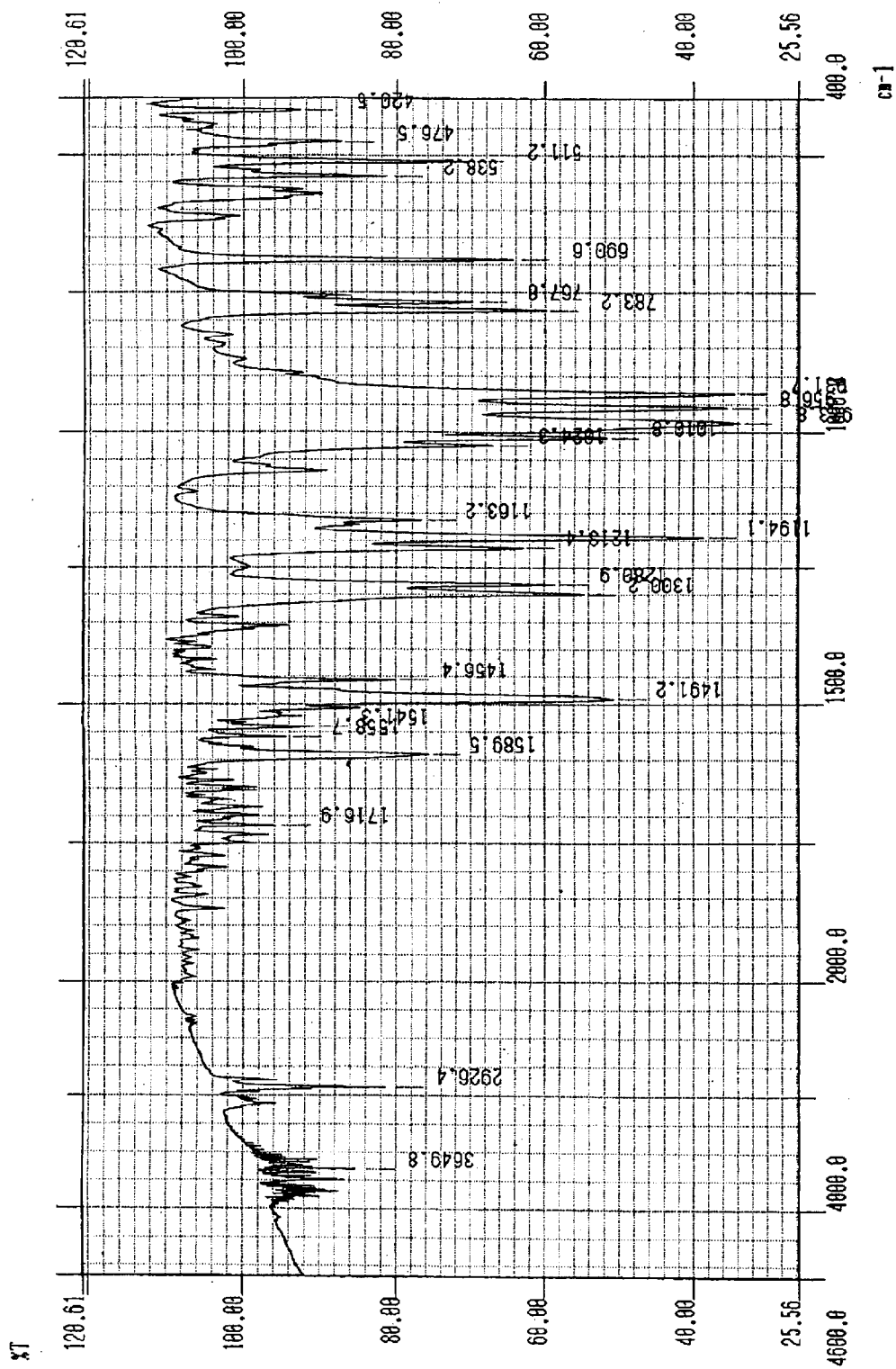
FIG. 2 is an infrared absorption spectrum for the adamantylbis(diphenylphosphate) obtained in Example A1.

The obtained oil was recrystallized with a mixed solvent of ethyl acetate (90 ml) and hexane (200 ml) to obtain adamantylbis(diphenylphosphate). The result of $^1H$ NMR is shown in FIG. 1, and the result of IR spectrum is shown in FIG. 2.

yield (weight): 106.5 g yield (ratio): 71%

$^1$H NMR (500 MH$_z$, CDCl$_3$, ppm): 7.33 to 7.15 (m, 20H), 2.48 (s, 2H), 2.39 (s, 2H), 2.13 to 2.04 (q, 8H), 1.52 (s, 2H)

IR spectrum (cm$^{-1}$): 2926, 1590, 1491 (benzene ring), 1300, 1281 (P=O), 1194 (P—O—C(aromatic)), 984(P—O—C), 957(P—O—C), 932(P—O—C)

Example A2

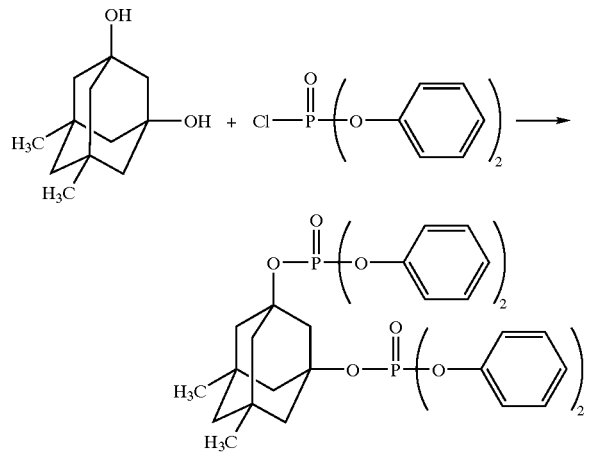

Dimethyladamantylbis(diphenylphosphate) was prepared according to the reaction scheme.

Into a three-neck flask (500 ml) equipped with a dropping funnel, a Dimroth condenser and a calcium chroride (CaCl$_2$) tube, were fed 42.2 g (215 mmol) of dimethyl adamantanediol and 213 g (2.69 mol) of pyridine, and 148 g (55.1 mmol) of diphenylphosphorochloridate was added dropwise to the mixture for 30 minutes at 60° C. with stirring. After dropping was completed, the reaction was effected at 90° C. for 7 hours.

The reaction mixture was cooled to room temperature, and 400 ml of ethyl acetate and 400 ml of water were added to the reaction mixture for extraction of an object compound. Further, an organic layer was washed with 400 ml of 2N (2 mol/L) hydrochloric acid three times, 400 ml of saturated sodium carbonate aqueous solution three times, and 400 ml of water one time in this order. The organic layer was dried with sodium sulfate and evaporated.

The resultant residue was dissolved in a mixed solvent of ethyl acetate (90 ml) and hexane (200 ml) and recrystallized from the solvent to obtain dimethyladamantylbis (diphenylphosphate).

yield (weight): 107 g yield (ratio): 75%

$^1$H NMR (500 MH$_z$, CDCl$_3$, ppm): 7.36 to 7.15 (m, 20H), 2.38 (s, 2H), 1.79 (s, 8H), 1.12 (s, 2H), 0.96 (s, 6H)

IR spectrum (cm$^{-1}$): 1592, 1489 (benzene ring), 1293 (P=O), 1194 (P—O—C(aromatic)), 994 (P—O—C), 951 (P—O—C), 932(P—O—C)

Example A3

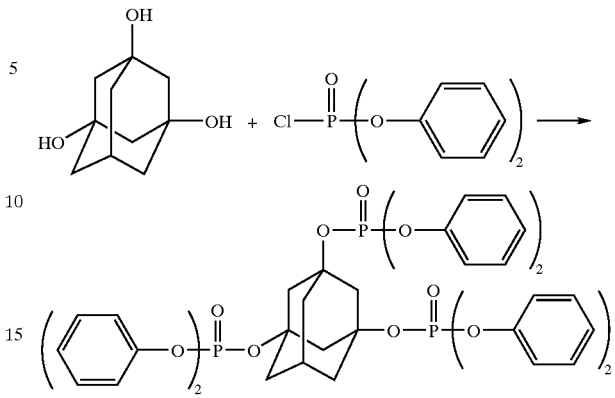

Adamantyltris(diphenylphosphate) was prepared according to the reaction scheme.

Into a three-neck flask (500 ml) equipped with a dropping funnel, a Dimroth condenser and a CaCl$_2$ tube were fed 20 g (109 mmol) of adamantanetriol and 150 g (1.9 mol) of pyridine, and 103 g (382 mmol) of diphenylphosphoric chloride was added dropwise to the mixture for 25 minutes at 70° C. under stirring. After dropping was completed, the reaction was effected under 90° C. for 7 hours.

The reaction mixture was cooled to room temperature, and 300 ml of dichloromethane was added to the reaction mixture for extracting an object compound. Further, the extract was washed with 170 ml of 2N (2 mol/L) hydrochloric acid three times, 300 ml of water one time, 300 ml of 15% by weight Na$_2$CO$_3$ aqueous solution two times, and 300 ml of water one time in this order. The organic layer was dried with sodium sulfate, and then solvents were evaporated to obtain the objective adamantyltris (diphenylphosphate) as light-yellow oil.

yield (weight): 81.3 g yield (ratio): 85%

IR spectrum (NEAT, cm$^{-1}$): 1593, 1491, 1289, 1217, 1190, 1163, 1103, 1019

$^1$H NMR (500 MH$_z$, CDCl$_3$, ppm): 7.31 to 7.14 (m, 30H), 2.55 to 2.48 (q, 7H), 2.03 (s, 6H)

Example B1

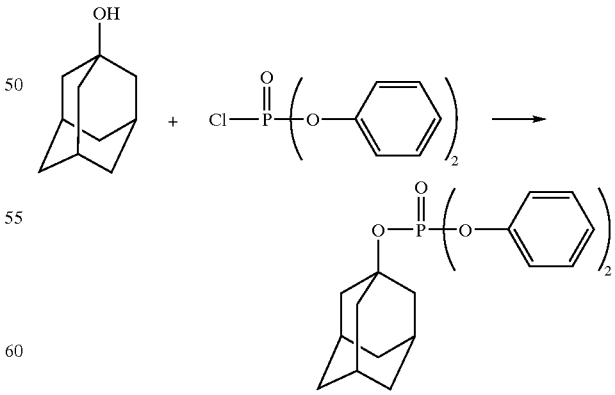

Adamantyldiphenylphosphate was prepared according to the reaction scheme.

Figure 3:
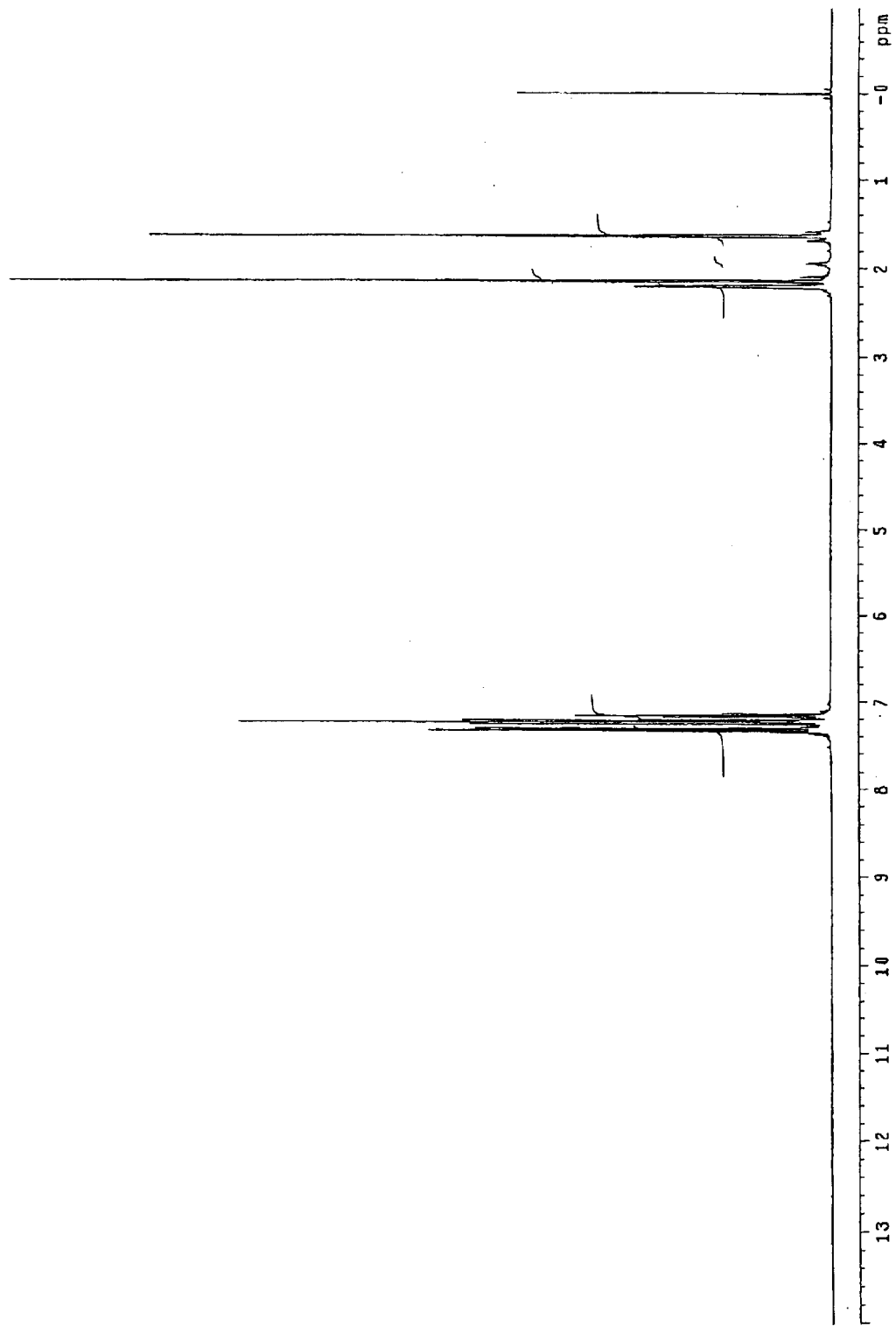
FIG. 3 is a $^1$H-NMR spectrum for the adamantyldiphenylphosphate obtained in Example B1.
Figure 4:
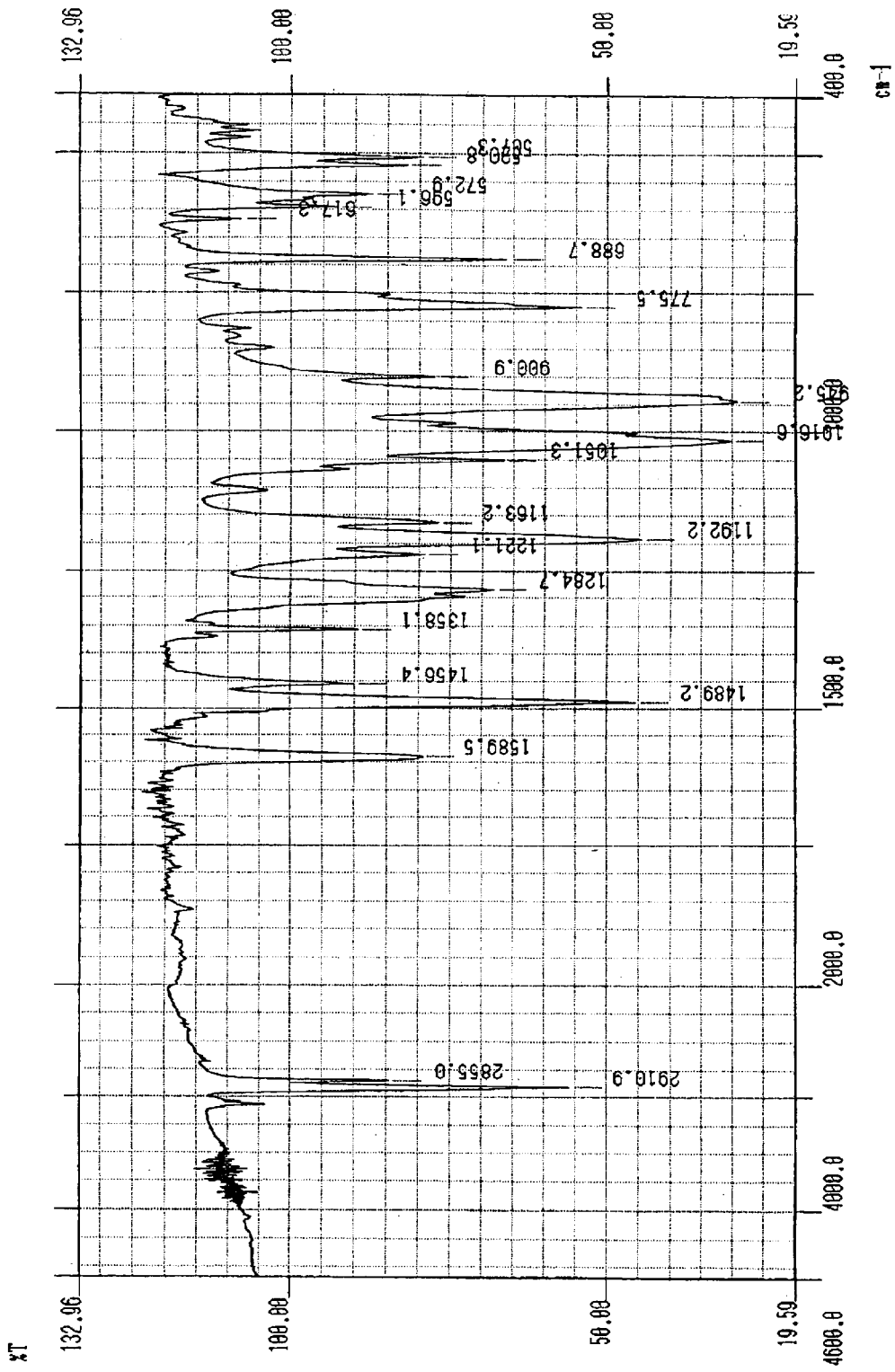
FIG. 4 is an infrared absorption spectrum for the adamantylbis(diphenylphosphate) obtained in Example B1.

Into a flask provided with a thermometer, a stirring equipment, a dropping funnel, a CaCl$_2$ tube, and a condenser, were fed 45 g (0.29 mol) of 1-adamantanol and 117 g (1.5 mol) of pyridine, and were stirred at 60° C. 95 g (0.35 mmol) of diphenylphosphoric chloride was added dropwise with vigorously stirring. After dropping was completed, the reaction was effected at 90° C. for 3 hours. After the reaction mixture was cooled to room temperature, 700 ml of ethyl acetate was added to the reaction mixture, and the mixture was washed with 700 ml of water two times, 700 ml of 1N (1 mol/L) hydrochloric acid three times, 700 ml of 15% by weight $Na_2CO_3$ aqueous solution three times, and 700 ml of water two times in this order. After an organic layer was dried with sodium sulfate and solvents were evaporated, the resultant residue was crystallized from a mixed solvent of ethyl acetate and hexane (1:2) to obtain the objective adamantyldiphenyl phosphate. The result of $^1$H NMR is shown in FIG. 3, and the result of IR spectrum is shown in FIG. 4.

yield (weight): 109 g yield (ratio): 97% purity: 98.6% (GC area ratio)

melting point: 47° C.

thermal decomposition temperature: 220° C.

mass spectroscopy: m/Z 384

$^1$H NMR (400 $MH_z$, $CDCl_3$, ppm): 7.35 to 7.16 (m, 10H, phenyl), 2.20 (s, 3H, bridgehead), 2.14 (d, 6H, 2-position, 8-position, 10-position), 1.63 (t, 6H, 4-position, 6-position, 9-position)

IR spectrum ($cm^{-1}$): 2910 to 2855, 1590, 1489, 1285, 1192, 1017, 945, 775, 688

Example B2

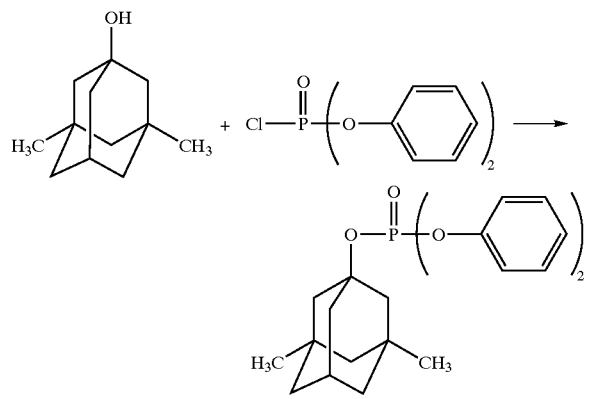

Dimethyladamantyldiphenylphosphate was prepared according to the reaction scheme.

Into a flask provided with a thermometer, a stirring equipment, a dropping funnel, a $CaCl_2$ tube, and a condenser were fed 28 g (0.16 mol) of dimethyl-1-adamantanol and 61 g (0.78 mol) of pyridine, and the mixture was stirred at 60° C. To the mixture, 50 g (0.19 mol) of diphenylphosphoric chloride was added dropwise under vigorously stirring. After dropping was completed, the reaction was effected at 90° C. for 3 hours. After the reaction mixture was cooled to room temperature, 300 ml of ethyl acetate was added to the reaction mixture, and the mixture was washed with 300 ml of water two times, 300 ml of 1N (1 mol/L) hydrochloric acid three times, 300 ml of 15% by weight $Na_2CO_3$ aqueous solution three times, and 300 ml of water two times in this order, and was dried with sodium sulfate. After solvents were evaporated, the residue was crystallized from a mixed solvent of ethyl acetate and hexane (1:2) to obtain the objective dimethyladamantyldiphenylphosphate.

yield (weight): 64 g yield (ratio): 99% purity: 96.7% (GC area ratio)

thermal decomposition temperature: 233° C.

$^1$H NMR (500 $MH_z$, $CDCl_3$, ppm): 7.33 (t, 2H, m-phenyl), 7.21 to 7.23 (m, 2H, o-phenyl), 7.16 (t, 1H, o-phenyl). 2.21 to 2.26 (m, 1H, bridgehead), 1.95 (d, 2H), 1.75 to 1.84 (q, 4H), 1.24 to 1.38 (q, 4H), 1.10 to 1.19 (m, 2H), 0.85 (s, 6H)

IR spectrum (NEAT, $cm^{-1}$): 2915, 1456, 1281, 1194, 1021, 953, 758

Example B3

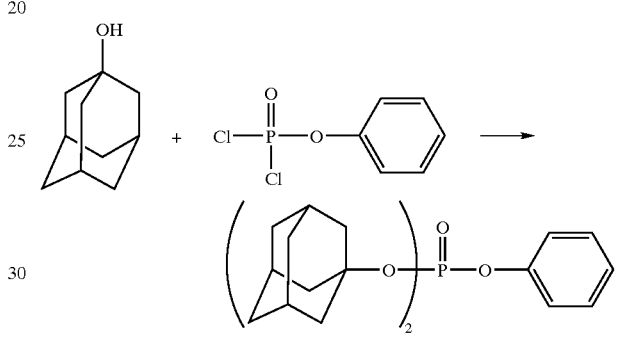

Bis(adamantyl)phenylphosphate was prepared according to the reaction scheme.

Into a three-neck flask (50 ml) equipped with a dropping funnel, a Dimroth condenser and a $CaCl_2$ tube, were fed 50 g (0.33 mol) of adamantanol and 126 g (1.6 mol) of pyridine, and the reaction mixture were stirred at 60° C. Into the reaction mixture was added dropwise 33 g (0.16 mol) of phenylphosphoric dichloride. After dropping was completed, the reaction was effected at 90° C. for 6 hours. After complete reaction, the reaction mixture was cooled to room temperature, and 500 ml of ethyl acetate was added to the reaction mixture, and the mixture was washed with 750 ml of water, 500 ml of 2N (2 mol/L) hydrochloric acid four times, 500 ml of water one time, 500 ml of 15% by weight $Na_2CO_3$ aqueous solution two times, and 500 ml of water one time in this order, and the organic layer was dried with sodium sulfate. After the solvent was evaporated, the resultant residue was crystallized from a mixed solvent of ethyl acetate and hexane (1:1.1) to obtain the objective bis(adamantyl)phenylphosphate.

yield (weight): 59 g yield (ratio): 85% melting point: 120° C.

thermal decomposition temperature: 253° C.

$^1$H NMR (500 $MH_z$, $CDCl_3$, ppm): 7.32 (t, 2H), 7.22 (d, 2H), 7.11 (t, 1H), 2.17 (s, 6H), 2.11 (d, 12H), 1.63 (s, 12H)

IR spectrum ($cm^{-1}$): 2911, 1489, 1264, 1215, 1069, 1009, 934

Example C1

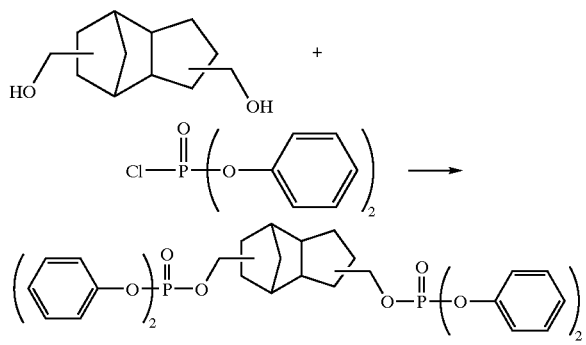

3,4- or 4,9-bis[(diphenylphosphoroxy)methyl]tricyclo [5.2.1.0$^{2,6}$]decane was prepared according to the above mentioned reaction scheme.

Into a three-neck flask (500 ml) equipped with a dropping funnel, a Dimroth condenser and a calcium chroride tube, were fed 53.8 g (0.27 mol) of tricyclo[5.2.1.0$^{2,6}$]decane-3,8- or 4,9-dimethanol (manufactured by Celanese Co. Ltd., USA) and 273 g (3.4 mol) of pyridine, and were stirred at 60° C. After 183 g (0.68 mol) of diphenylphosphoro chloridate was added dropwise into the reaction mixture for 30 minutes, the reaction was effected at 90° C. for 6 hours to complete the reaction.

The reaction mixture was cooled to room temperature, and an object was extracted with 500 ml of ethyl acetate. An organic layer was washed with water, 2N (2 mol/L) hydrochloric acid, water, 15% by weight $Na_2CO_3$ aqueous solution, and water in this order, was dried with sodium sulfate, and the solvent was evaporated to obtain the object compound as light-yellow oil.

yield (weight): 173.8 g yield (ratio): 96% purity: 98% (High Performance Liquid Chromatography (HPLC) area ratio)

melting point: 117° C.

thermal decomposition temperature: 277° C.

IR spectrum (NEAT, cm$^{-1}$): 3009, 2955, 1592, 1491, 1287, 1192, 1024, 957, 689

$^1$H NMR (400 MH$_z$, CDCl$_3$, ppm): 7.36 to 7.16 (m, 20H), 4.10 to 3.96 (m, 4H), 2.49 to 2.21 (m, 3H), 2.15 to 1.95 (m, 3H), 1.74 to 1.18 (m, 7H), 0.95 to 0.84 (m, 1H)

Example C2

(4R,8S)-bis(diphenylphosphoroxymethyl)-(1R,2S,6R, 7R)-tricyclo[5.2.1.0$^{2,6}$]decane was isolated by the following method.

The oil obtained by the Example C1 mentioned above was recrystallized from a mixed solvent of ethyl acetate and hexane to obtain (4R,8S)-bis(diphenylphosphoroxy methyl)-(1R,2S,6R,7R)-tricyclo[5.2.1.0$^{2,6}$]decane as white crystal. The obtained white crystal was analyzed by HPLC, and one peak was found at 18.2 minutes. The structure was determined by $^1$H NMR spectrum, $^{13}$C NMR spectrum, DEPT spectrum, COSY spectrum, and HETCOR spectrum. The yield of the recrystal was 25%.

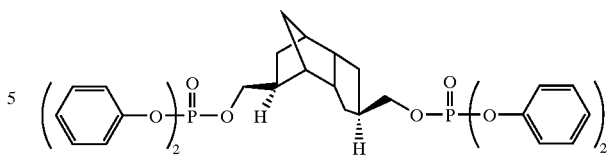

melting point: 91° C.

thermal decomposition temperature: 264° C.

IR spectrum (cm$^{-1}$): 2957, 1592, 1489, 1293, 1190, 1040, 1011, 954, 939, 777, 760, 691

$^1$H NMR (500 MH$_z$, CDCl$_3$, ppm): 7.36 to 7.16 (m, 20H), 4.10 to 4.06 (m, 2H), 3.99 to 3.94 (m, 2H), 2.49 to 2.38 (m, 2H), 2.32 to 2.21 (m, 1H), 2.10 (s, 1H), 2.05 (d, 1H), 2.03 to 1.95 (m, 1H), 1.64 to 1.61 (m, 2H), 1.56 to 1.49 (m, 1H), 1.37 (q, 2H), 1.27 to 1.21 (m, 2H), 0.92 to 0.85 (m, 1H)

(Analysis Condition of HPLC)

column (manufactured by YMC, J'sphere ODS-M80 JM08S04-2546WT; 250 mm×4.6 mm), eluate (acetonitrile:water=60:40), flow rate (0.8 mL/minute), wavelength of measurement (260 nm), temperature of column oven (40° C.)

Example D1

Into a three-neck flask (1000 ml) equipped with a dropping funnel and a calcium chroride tube, were fed 25.4 g (0.18 mol.) of p-xylyleneglycol, 190.8 g of acetonitrile, and 50.9 g (0.64 mol) of pyridine, and the reaction mixture was stirred at 3.5° C. Into the reaction system, 98.8 g (0.37 mol) of diphenylphosphoric chloride was added dropwise for 45 minutes, and the reaction was effected at 2.0 to 9.5° C. for 1.5 hours to complete the reaction. Complete consumption of p-xylyleneglycol of raw material was determined by HPLC.

The reaction mixture was put into 1300 g of ice water, and the object compound was deposited and was filtered. The object compound was washed with 200 ml of cool methanol, and was filtered. The objective p-xylyleneglycolbis (diphenylphosphate) was recrystalized from 200 ml acetonitrile to be purified.

yield (weight): 99.6 g yield (ratio): 90% purity: 95% (HPLC area ratio)

melting point: 101° C. (thermal decomposition temperature: 241° C.)

(Analysis Condition of HPLC)

column (manufactured by YMC, J'sphere ODS-M80 JM08S04-2546WT, 250 mm×4.6 mm), eluate (acetonitrile:water=60:40 to 80:20), flow rate (0.8 mL/min), wavelength of measurement (254 nm), temperature of column oven (40° C.)

IR spectrum (cm$^{-1}$): 1590, 1489, 1293, 1192, 1015, 957, 816, 777, 691, 532, 504

$^1$H NMR (400 MH$_z$, CDCl$_3$, ppm): 7.33 to 7.16 (m, 24H), 5.25 to 5.24 (d, 4H)

Example D2

Into a three-neck flask (1000 ml) equipped with a dropping funnel and a calcium chroride tube, were fed 35.1 g (0.25 mol) of o-xylyleneglycol, 160.2 g of acetonitrile, 70.3 g (0.89 mol) of pyridine, and 136.3 g (0.51 mol) of diphenylphosphoric chloride, and the reaction was effected by a method similar to the method of Example 1, and a reaction product was purified by column chromatography to obtain the objective o-xylyleneglycolbis(diphenylphosphate) as colorless liquid.

yield (weight): 140.8 g yield (ratio): 92% purity: 98% (HPLC area ratio)

thermal decomposition temperature: 225° C.

IR spectrum (cm$^{-1}$) 1590, 1489, 1291, 1217, 1190, 1161, 1011, 953, 754, 689

$^1$H NMR (400 MH$_z$, CDCl$_3$, ppm): 7.40 to 7.09 (m, 24H), 5.25 to 5.24 (d, 4H)

Example D3

Into a three-neck flask (1000 ml) equipped with a dropping funnel and a calcium chroride tube, were fed 50.0 g (0.36 mol) of m-xylyleneglycol, 372.7 g of acetonitrile, 100.2 g (1.3 mol) of pyridine, and 194.7 g (0.73 mol) of diphenylphosphoric chloride, and the reaction was effected by a method similar to the method of Example 1, and a reaction product was purified by column chromatography to obtain the objective m-xylyleneglycolbis (diphenylphosphate).

yield (weight): 196.2 g yield (ratio): 90% purity: 97% (HPLC area ratio)

IR spectrum (cm$^{-1}$) 1590, 1487, 1289, 1215, 1188, 1155, 1024, 1010, 947, 754, 689

$^1$H NMR (400 MH$_z$, CDCl$_3$, ppm): 7.34 to 7.15 (m, 24H), 5.21 to 5.19 (d, 4H)

Comparative Example D1

Into a three-neck flask (100 ml) equipped with a dropping funnel, a Dimroth condenser and calcium chroride tube, were fed 2.5 g (18 mmol) of p-xylyleneglycol, 19 g of acetonitrile, and 5.1 g (64 mmol) of pyridine, and the reaction mixture was stirred at room temperature. After 9.9 g (37 mmol) of diphenylphosphate was added dropwise into the reaction system for 30 minutes, the reaction was effected at 68° C. for 1.5 hours to complete the reaction.

The reaction mixture was analyzed by HPLC, and the peak corresponding to the objective compound was not found.

Example E1

2,5-bis(diphenylphosphoroxymethyl)norbornane was prepared according to the above reaction scheme.

Into a three-neck flask (300 ml) equipped with a dropping funnel, a Dimroth condenser and a CaCl$_2$ tube, were fed 19.3 g (147 mmol) of norbornanedimethanol and 147 g (1.86 mol) of pyridine, and 83.1 g (309 mmol) of diphenylphosphoric chloride was added dropwise for 30 minutes at 60° C. with stirring. After dropping was completed, the reaction was effected at 90° C. for 4 hours.

The reaction mixture was cooled to room temperature, and an object compound was extracted with 300 ml of dichloromethane, and an organic layer was washed with 170 ml of 2N (2 mol/L) hydrochloric acid three times, 300 ml of water one time, 300 ml of 15% by weight Na$_2$CO$_3$ aqueous solution two times, and 300 ml of water one time in this order. After the organic layer was dried with sodium sulfate, the solvent was evaporated to obtain the objective 2,5-bis (diphenyl phosphoroxymethyl)norbornane.

yield (weight): 70.6 g yield (ratio): 92%

IR spectrum (cm$^{-1}$): 2953, 1590, 1489, 1456, 1296, 1217, 1192, 1163, 1021. 953, 776, 766, 691

$^1$H NMR (500 MH$_z$, CDCl$_3$, ppm): 7.33 to 7.21 (m, 20H), 4.24 to 3.95 (m, 4H), 2.23 to 0.65 (m, 10H)

Example E2

2,3-dihydroxynorbornane of a raw material for an objective compound was prepared according to the above reaction scheme.

Into a four-neck flask (200 ml) were fed 20.3 g (185 mmol) of 2,3-epoxynorbornane, 50 ml of water, 25 ml of acetone, and 50 µl of sulfuric acid, and the reaction mixture was refluxed at 40° C. for 6 hours. After complete reaction, an object compound was extracted with each 40 ml of diethylether five times, and the resultant extract was washed with saturated salt solution (braine), and was dried with sodium sulfate to obtain 2,3-dihydroxynorbornane.

yield (weight): 20.5 g yield (ratio): 87%

After that, 2,3-bis(diphenylphosphoroxy)norbornane was prepared according to the reaction scheme.

Into a three-neck flask (300 ml) equipped with a dropping funnel, a Dimroth condenser and a CaCl$_2$ tube, were fed 10.0 g (78.2 mmol) of 2,3-dihydroxynorbornane and 61.7 g (780 mmol) of pyridine, and 52.4 g (195 mmol) of diphenylphosphoric chloride was added dropwise for 50 minutes at 60° C. with stirring. After dropping was completed, the reaction was effected at 90° C. for 6 hours.

The reaction mixture was cooled to room temperature, and an object compound was extracted with 300 ml of dichloromethane, and an organic layer was washed with 170 ml of 2N (2 mol/L) hydrochloric acid three times, 300 ml of water one time, 300 ml of 15% by weight $Na_2CO_3$ aqueous solution two times, and 300 ml of water one time in this order. The organic layer was dried with sodium sulfate, and the solvent was evaporated to obtain light-yellow oil. The oil was subjected to column chromatography (an eluate was ethyl acetate/hexane=5/3) to isolate the objective 2,3-bis(diphenylphosphoroxy)norbornane.

yield (weight): 36.5 g yield (ratio): 79%

IR spectrum (NEAT, $cm^{-1}$): 1592, 1489, 1283, 1217, 1190, 1163, 1084, 1063, 1026, 1011

$^1$H NMR (400 $MH_z$, $CDCl_3$, ppm): 7.32 to 7.13 (m, 20H), 4.77 to 4.73 (m, 2H), 2.57 (d, 1H), 2.39 (s, 1H), 2.16 (d, 1H), 2.03 to 1.97 (q, 1H), 1.66 to 1.55 (m, 2H), 1.19 to 1.08 (m, 2H)

Example E3

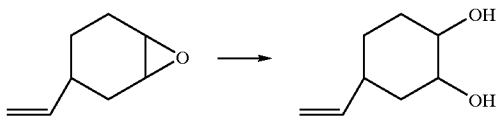

1,2-dihydroxy-4-vinylcyclohexane of a raw material for an objective compound was prepared according to the reaction scheme.

Into a two-neck flask (100 ml) were fed 15.9 g (128 mmol) of 4-vinylcyclohexene-1,2-epoxide, 40 ml of water, 20 ml of acetone, and 40 µl of sulfuric acid, and the reaction mixture was refluxed at 75° C. for 4 hours. After complete reaction, an object compound was extracted with each 60 ml of diethylether four times, and was washed with saturated salt solution, and then was dried with sodium sulfate. The solvent was evaporated to obtain 1,2-dihydroxy-4-vinylcyclohexane.

yield (weight): 16.4 g yield (ratio): 90%

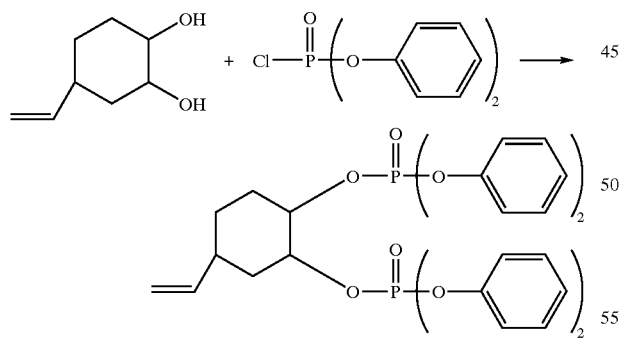

After that, 1,2-bis(diphenylphosphoroxy)-4-vinylcyclohexane was prepared according to the above reaction scheme. Into a three-neck flask (300 ml) equipped with a dropping funnel, a Dimroth condenser and a $CaCl_2$ tube, were fed 9.9 g (69.6 mmol) of 1,2-dihydroxy-4-vinylcyclohexane and 55.6 g (703 mmol) of pyridine, and 46.9 g (175 mmol) of diphenylphosphoric chloride was added dropwise for 15 minutes at 60° C. with stirring. After dropping was completed, the reaction was effected at 90° C. for 6 hours.

The reaction mixture was cooled to room temperature, and an object compound was extracted with 300 ml of dichloromethane, and an organic layer was washed with 150 ml of 2N (2 mol/L) hydrochloric acid three times, 300 ml of water one time, 300 ml of 15% by weight $Na_2CO_3$ aqueous solution two times, and 300 ml of water one time in this order. The organic layer was dried with sodium sulfate, and then the solvent was evaporated to obtain light-yellow oil. The oil was subjected to column chromatography (eluates were dichloromethane and ethyl acetate) to isolate the objective 1,2-bis(diphenylphosphoroxy)-4-vinylcyclohexane.

yield (weight): 35.7 g yield (ratio): 84%

IR spectrum (NEAT, $cm^{-1}$) 1592, 1489, 1287, 1227, 1190, 1163, 1046, 1024, 1011

$^1$H NMR (400 $MH_z$, $CDCl_3$, ppm): 7.34 to 7.15 (m, 20H), 5.70 to 5.61 (m, 1H), 4.97 to 4.92 (m, 2H), 4.87 to 4.85 (m, 1H), 4.84 to 4.75 (m, 1H), 2.34 to 2.30 (m, 1H), 1.91 to 1.85 (m, 3H), 1.73 to 1.67 (t, 1H), 1.56 to 1.51 (m, 1H), 1.47 to 1.40 (m, 1H)

Example E4

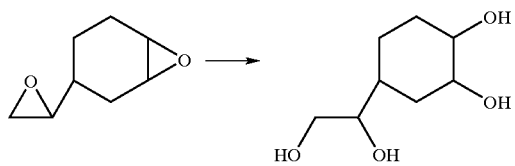

1,2-dihydroxy-4-(1',2'-dihydroxyethyl)cyclo hexane of raw material for an object compound was prepared according to the reaction scheme.

Into a two-neck flask (100 ml) were fed 20.0 g (143 mmol) of 4-vinylcyclohexene dioxide, 50 ml of water, 25 ml of acetone, and 50 µl of sulfuric acid, and the reaction was effected at room temperature for 4 hours.

After complete reaction, the reaction mixture was neutralized with 10% by weight sodium carbonate aqueous solution, and the solvent was evaporated to obtain 1,2-dihydroxy-4-(1',2'-dihydroxyethyl)cyclohexane.

yield (weight): 23.4 g yield (ratio): 93%

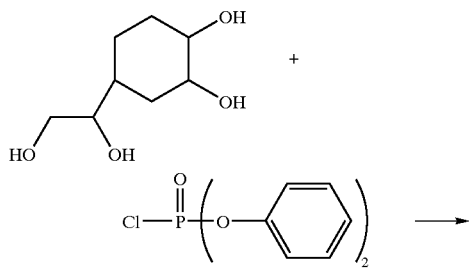

-continued

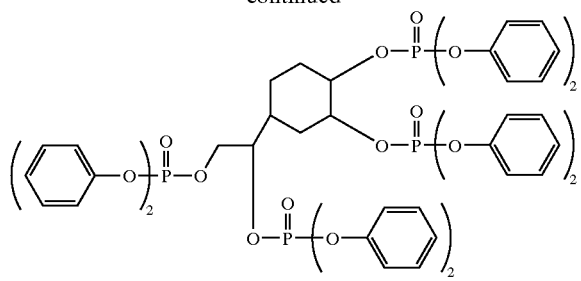

After that, 1,2-bis(diphenylphosphoroxy)-4-[1',21-bis(diphenylphosphoroxy)ethyl]cyclohexane was prepared according to the reaction scheme.

Into a three-neck flask (300 ml) equipped with a dropping funnel, a Dimroth condenser and a CaCl$_2$ tube, were fed 10.0 g (56.6 mmol) of 1,2-dihydroxy-4-(1',2'-dihydroxyethyl)cyclohexane and 68.3 g (863 mol) of pyridine, and 76.3 g (284 mmol) of diphenylphosphoric chloride was added dropwise for 30 minutes at 60° C. with stirring. After dropping was completed, the reaction was effected at 90° C. for 6 hours.

The reaction mixture was cooled to room temperature, and an object compound was extracted with 300 ml of dichloromethane, and an organic layer was washed with 170 ml of 2N (2 mol/L) hydrochloric acid three times, 300 ml of water one time, 300 ml of 15% by weight Na$_2$CO$_3$ aqueous solution two times, and 300 ml of water one time in this order. The organic layer was dried with sodium sulfate, and then the solvent was evaporated to obtain light-yellow oil. The oil was subjected to column chromatography to isolate the object compound.

yield (weight): 57.53 g yield (ratio): 92%

$^1$H NMR (400 MH$_z$, CDCl$_3$, ppm): 7.37 to 7.15 (m, 40H), 4.92 to 3.54 (m, 5H), 2.32 to 1.41 (m, 7H)

Example E5

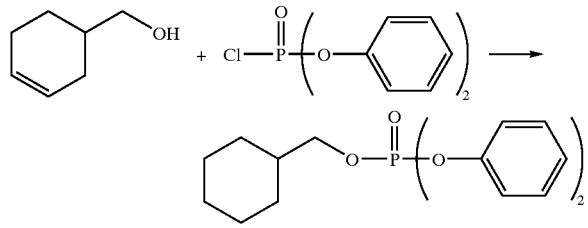

1-diphenylphosphoroxymethyl-3-cyclohexene was prepared according to the reaction scheme.

Into a three-neck flask (500 ml) equipped with a dropping funnel, a Dimroth condenser and a CaCl$_2$ tube, were fed 12.0 g (107 mmol) of 3-cyclohexen-1-methanol and 46.5 g (588 mmol) of pyridine, and 31.6 g (118 mmol) of diphenylphosphoric chloride was added dropwise for 30 minutes at room temperature with stirring. After dropping was completed, the reaction was effected at 60° C. for 5 hours.

The reaction mixture was cooled to room temperature, and an object compound was extracted with 300 ml of dichloromethane, and an organic layer was washed with 150 ml of water one time, 150 ml of 2N (2 mol/L) hydrochloric acid two times, 150 ml of water one time, 150 ml of 10% by weight Na$_2$CO$_3$ aqueous solution two times, and 50 ml of water one time in this order. The organic layer was dried with sodium sulfate, and then the solvent was evaporated to obtain the object compound as colorless liquid.

yield (weight): 40.0 g yield (ratio): 85%

IR spectrum (NEAT, cm$^{-1}$): 1585, 1480, 1287, 1189, 1163, 1051, 1022, 1010

$^1$H NMR (500 MH$_z$, CDCl$_3$, ppm): 7.35 to 7.16 (m, 10H), 6.10 to 6.01 (m, 2H), 4.16 to 4.10 (t, 2H), 2.11 to 1.96 (m, 4H), 1.77 to 1.71 (m, 2H), 1.35 to 1.29 (m, 1H)

Example E6

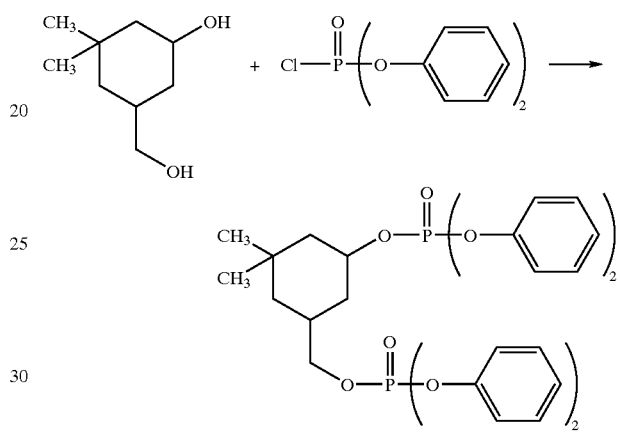

3,3-dimethyl-5-(diphenylphosphoroxymethyl)cyclohexylphosphate was prepared according to the reaction scheme.

Into a three-neck flask (200 ml) equipped with a dropping funnel, a Dimroth condenser and a CaCl$_2$ tube, were fed 7.0 g (44 mmol) of 3-hydroxymethyl-5,5-dimethylcyclo hexanol and 36.2 g (457 mol) of pyridine, and 29.8 g (111 mmol) of diphenylphosphoric chloride was added dropwise for 30 minutes at 60° C. with stirring. After dropping was completed, the reaction was effected at 90° C. for 4 hours.

The reaction solution was cooled to room temperature, and an object compound was extracted with 300 ml of dichloromethane, and an organic layer was washed with 170 ml of 2N (2 mol/L) hydrochloric acid three times, 300 ml of water one time, 300 ml of 15% by weight Na$_2$CO$_3$ aqueous solution two times, and 300 ml of water one time in this order. The organic layer was dried with sodium sulfate, and then the solvent was evaporated to obtain the objective 3,3-dimethyl -5-(diphenylphosphoroxymethyl)cyclohexylphosphate.

yield (weight): 24.6 g yield (ratio): 96%

IR spectrum (NEAT, cm$^{-1}$): 3011, 2957, 1592, 1491, 1458, 1283, 1227, 1190, 1163, 1024, 1011, 1001

$^1$H NMR (400 MH$_z$, CDCl$_3$, ppm): 7.36 to 7.14 (m, 20H), 5.03 to 4.99 (m, 1H), 4.03 to 4.00 (t, 2H), 2.10 (br, 1H), 1.99 to 1.95 (d, 1H), 1.80 to 1.76 (q, 1H), 1.67 (s, 1H), 1.44 to 1.40 (q, 1H), 1.28 to 1.24 (m, 1H), 1.22 to 1.14 (m, 1H), 0.92 (s, 3H), 0.85 (s, 3H)

Example F1

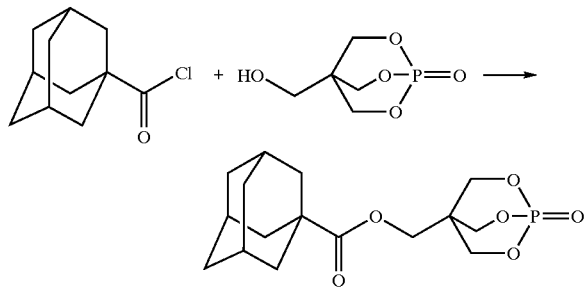

(1-oxo-2,6,7-trioxa-1-phosphabicyclo[2.2.2]-oct-4-yl) methyl adamantanecarbonate was prepared according to the reaction scheme.

Into a three-neck flask (500 ml) equipped with a dropping funnel, a Dimroth condenser and a CaCl$_2$ tube, were fed 59 g (0.33 mol) of 2,6,7-trioxa-1-phosphabicyclo2.2.2]octane-4-hydroxymethyl-1-oxide and 126 g (1.6 mol) of pyridine, and the reaction mixture was stirred at 60° C. Into the reaction mixture was added dropwise 80 g (0.40 mol) adamantanecarboxylic chloride dissolved in 100 ml of acetonitrile, and the reaction was effected at 85° C. for 5 hours.

Figure 5:
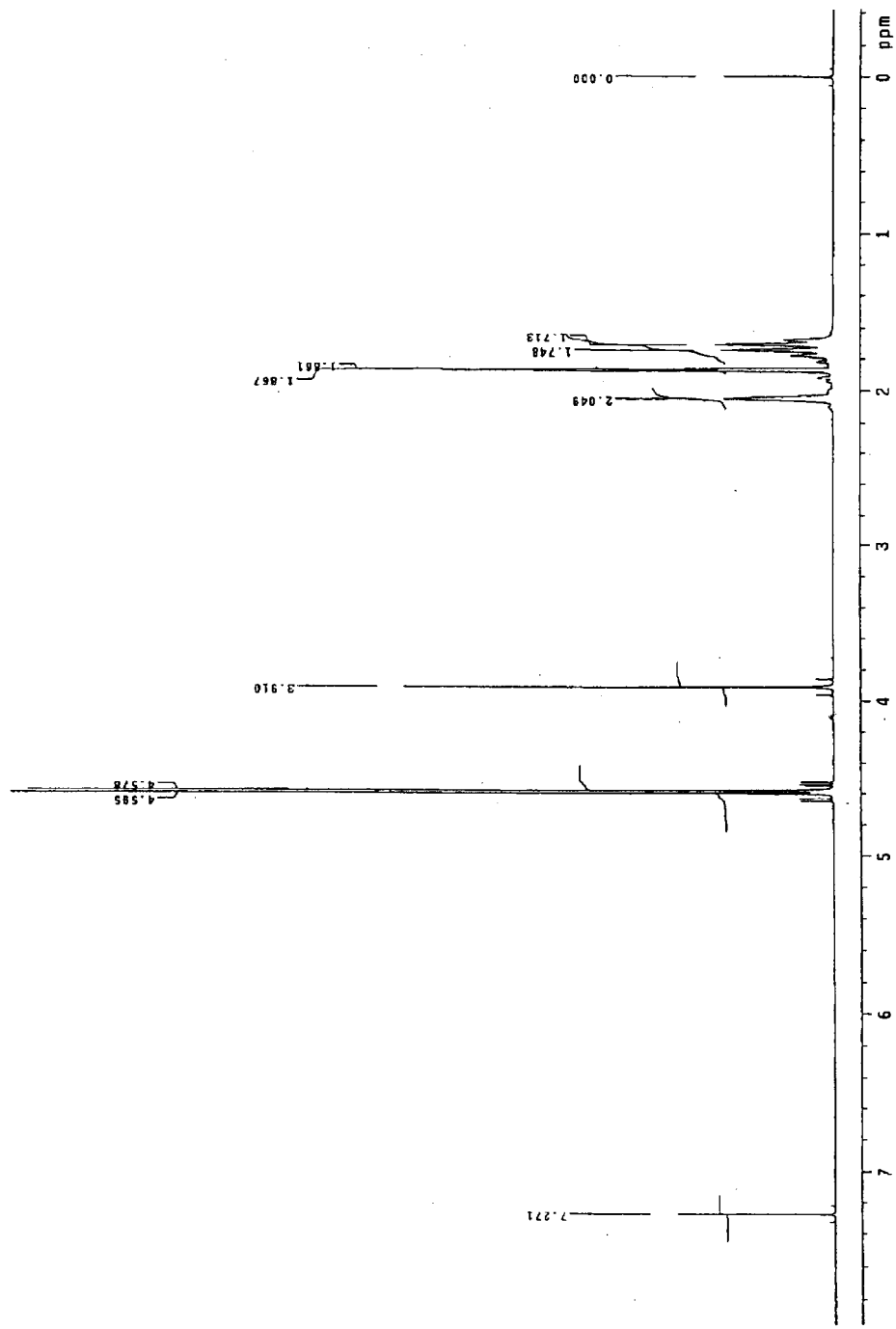
FIG. 5 is a $^1$H-NMR spectrum for the (1-oxo-2,6,7-trioxa-1-phosphabicyclo[2.2.2]-oct-4-yl)methyladamantanecarbonate obtained in Example F1.
Figure 6:
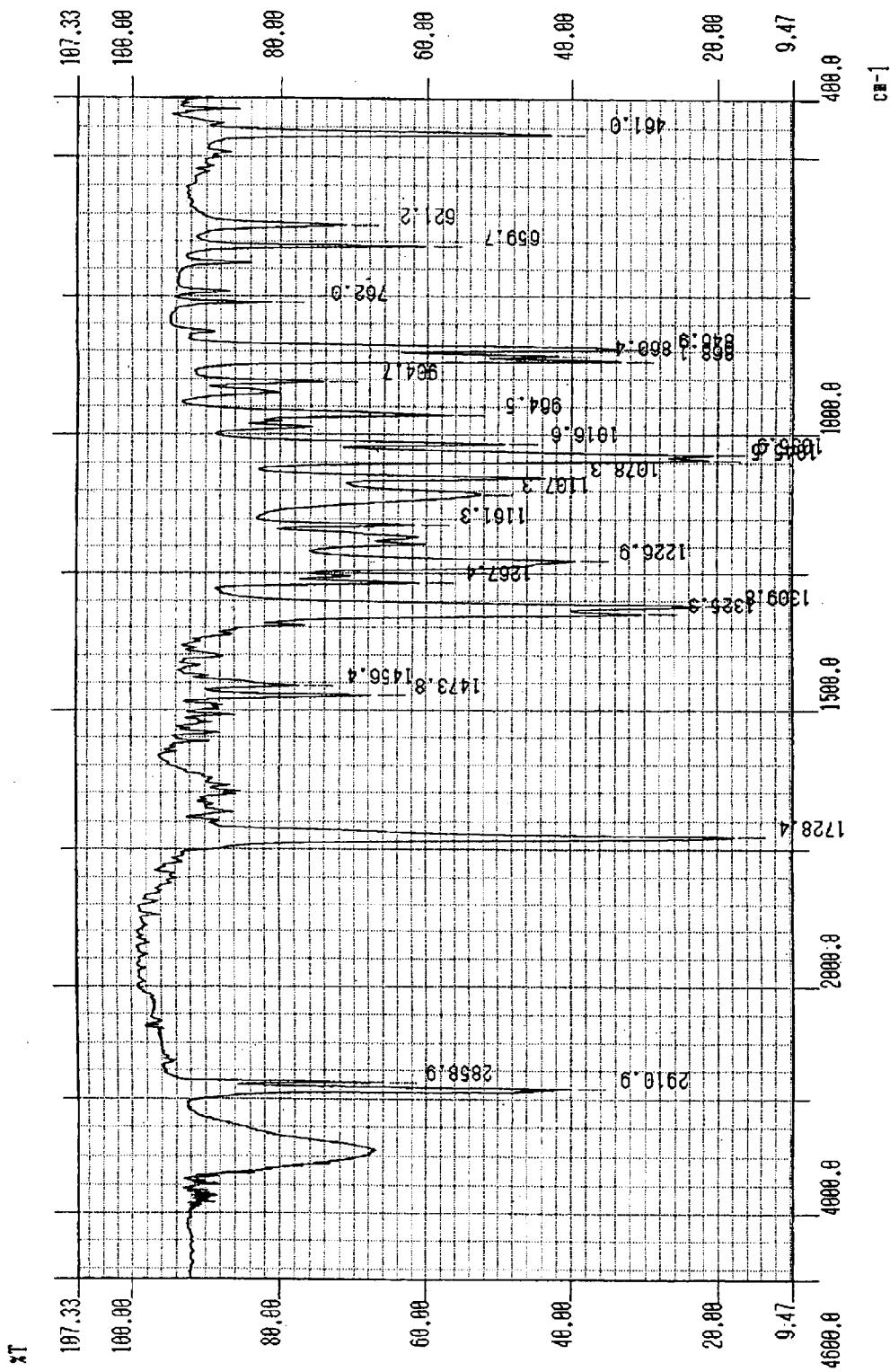
FIG. 6 is an infrared absorption spectrum for the (1-oxo-2,6,7-trioxa-1-phosphabicyclo[2.2.2]-oct-4-yl)methyladamantanecarbonate obtained in Example F1.

The reaction mixture was cooled to room temperature, and 500 ml of ethyl acetate and 500 ml of water was added to the reaction mixture, and the mixture was put into a separatory funnel to isolate an organic layer. The organic layer was washed with 500 ml of water one time, 500 ml of 15% by weight Na$_2$CO$_3$ aqueous solution two times, and 500 ml of water one time in this order. The organic layer was dried with sodium sulfate, and then the solvent was evaporated to obtain white solid. The resultant solid was washed with methanol and was dried under vacuum. The result of $^1$H NMR is shown in FIG. 5, and the result of IR spectrum is shown in FIG. 6.

yield (weight): 90 g
yield (ratio): 83%
$^1$H NMR (CDCl$_3$, 400 MH$_z$, δppm): 4.59 (d, 6H), 3.91 (d, 2H), 2.05 (s, 3H), 1.86 (d, 6H), 1.73 (q, 6H)
IR spectrum: 2910, 1728, 1325, 1310, 1227, 1046, 1036, 868, 847 (cm$^{-1}$)

Example F2

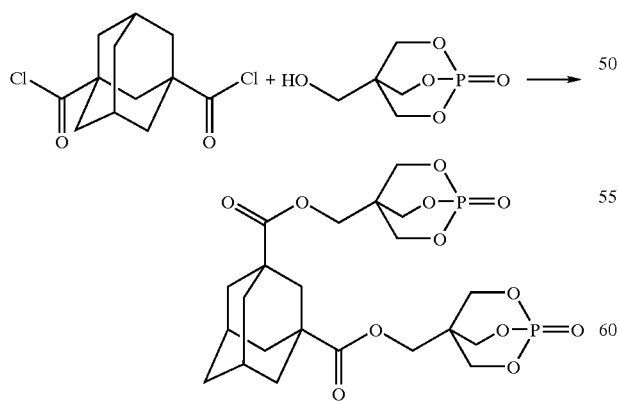

Bis(1-oxo-2,6,7-trioxa-1-phosphabicyclo[2.2.2]-oct-4-yl) methyl adamantanecarbonate was prepared according to the reaction scheme.

Into a three-neck flask (500 ml) equipped with a dropping funnel, a Dimroth condenser and a CaCl$_2$ tube, were fed 86 g (0.48 mol) of 2,6,7-trioxa-1-phosphabicyclo[2.2.2]octane-4-hydroxymethyl-1-oxide and 76 g (0.96 mol) of pyridine, and the reaction mixture was stirred at 60° C. Into the reaction mixture was added dropwise 50 g (0.19 mol) adamantanedicarboxylic dichloride dissolved in 100 ml of acetonitrile, and the reaction was effected at 85° C. for 8 hours.

The reaction mixture was cooled to room temperature, and 500 ml of ethyl acetate and 500 ml of water were added to the reaction mixture, and the mixture was put into a separatory funnel to isolate an organic layer. The organic layer was washed with 500 ml of water one time, 500 ml of 15% by weight Na$_2$CO$_3$ aqueous solution two times, and 500 ml of water one time in this order. The organic layer was dried with sodium sulfate, and the solvent was evaporated to obtain white solid. The obtained solid was washed with methanol and was dried under vacuum.

yield (weight): 88 g
yield (ratio): 84%
$^1$H NMR (CDCl$_3$, 400 MH$_z$, δppm) 4.61 (d, 12H), 4.02 (d, 4H), 2.48 (s, 2H), 2.39 (s, 2H), 2.09 (q, 8H), 1.51 (s, 2H)

What is claimed is:

1. A phosphorus-containing compound represented by the following formula (I), (II) or (III):

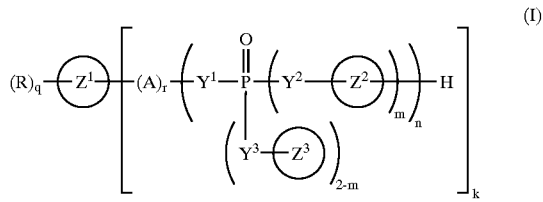

(I)

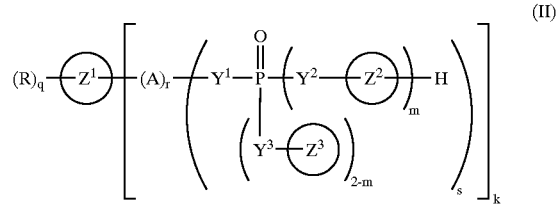

(II)

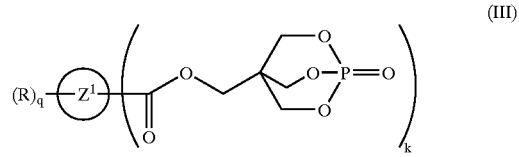

(III)

wherein $Z^1$, $Z^2$ and $Z^3$ are the same or different, each representing a cycloalkane ring, a cycloalkene ring, a polycyclic aliphatic hydrocarbon ring or an aromatic hydrocarbon ring, in which these rings may have a substituent; R represents a halogen atom, a hydroxyl group, a carboxyl group, a halocarboxyl group, an alkyl group, an alkoxy group, an alkenyl group or an aryl group; A represents a polyvalent group corresponding to an alkane; $Y^1$, $Y^2$ and $Y^3$ are the same or different, each representing —O—, —S— or —NR$^1$—
wherein R$^1$ represents a hydrogen atom or an alkyl group; k represents an integer of 1 to 6; m represents an integer of 0 to 2; n represents an integer of not less than 1; q represents an integer of 0 to 5; r represents 0 or 1; s represents an integer of 1 to 4; and
provided that when $Z^1$ is a cyclohexane ring, q is 0, and k is 1, factor r for A is 1; when $Z^1$ is a cyclohexane ring, q is 0, and k is 2 to 6, at least one of plural factors r for A is 1; when $Z^1$ is a benzene ring and k is 1, the factor r for A is 1; when $Z^1$ is a benzene ring and k is 2 to 6, at least one of plural factors r for A is 1; and bis((1-oxo-2,6,7-trioxa-1-phosphabicyclo[2.2.2]-oct-4-yl)methyl) 2,5-dibromoterephthalate, 1,4-cyclohexanedimethanol bis(diaryl phosphate), (1-oxo-2,6,7-trioxa-1-phosphabicyclo[2.2.2]-oct-4-yl)methyl benzoate, (1-oxo-2,6,7-trioxa-1-phosphabicyclo[2.2.2]-oct-4-yl)methyl cyclohexanecarboxylate, tris (tricyclo[5.2.1.0$^{2,6}$]decane)phosphate, 2-carboxy-3-diphenylphosphoroxynorbornane, and 3-diphenylphosphoroxynorbornane are excluded.

2. A phosphorus-containing compound according to claim 1, wherein the rings $Z^1$, $Z^2$ and $Z^3$ each is a dicyclic or tricyclic aliphatic hydrocarbon ring.

3. A phosphorus-containing compound according to claim 1, wherein the ring $Z^1$ is a norbornane ring, an adamantane ring, a tricyclo[5.2.1.0$^{2,6}$]decane ring, or a benzene ring, and the rings $Z^2$ and $Z^3$ each is an adamantane ring or a benzene ring.

4. A phosphorus-containing compound according to claim 1, wherein R is a halogen atom, a hydroxyl group, a $C_{1-4}$alkyl group, or a $C_{1-4}$alkoxy group in the formula (I).

5. A phosphorus-containing compound according to claim 1, wherein each $Y^1$, $Y^2$ and $Y^3$ represents —O—.

6. A phosphorus-containing compound according to claim 1, wherein k is an integer of 1 or 2, n is 1, and q is an integer of 0 to 2.

7. A phosphorus-containing compound according to claim 1, wherein a phosphorus-containing compound of the formula (I) is represented by the following formula (Ia):

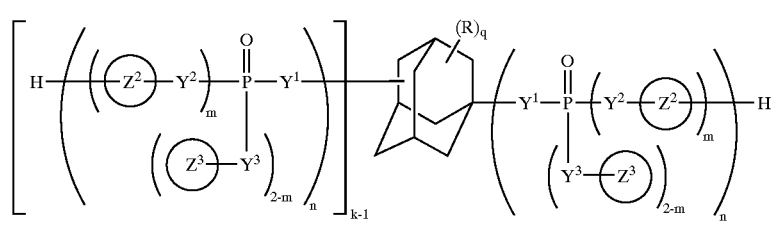

wherein the $Z^2$, $Z^3$, R, $Y^1$, $Y^2$, $Y^3$, k, m, n and q have the same meanings as defined above.

8. A phosphorus-containing compound according to claim 7, wherein, in the formula (Ia), $Z^2$ and $Z^3$ are the same or different, each representing a benzene ring or an adamantane ring in which these rings may have a substituent; R is a halogen atom, a hydroxyl group, a $C_{1-6}$ alkyl group, or a $C_{1-6}$ alkoxy group; $Y^1$, $Y^2$ and $Y^3$ each is —O— or —NR$^1$— (wherein R$^1$ represents a hydrogen atom or a $C_{1-4}$alkyl group)); k is an integer of 2 to 4; n is an integer of 1 to 3; and q is an integer of 0 to 4.

9. A phosphorus-containing compound according to claim 7, wherein, in the formula (Ia), $Z^2$ and $Z^3$ are the same or different, each representing a benzene ring which may have a substituent; R is a $C_{1-4}$alkyl group; n is 1; and q is an integer of 0 to 2.

10. A phosphorus-containing compound according to claim 7, wherein a compound represented by the formula (Ia) is an adamantyl bis, tris or tetrakis-(di $C_{6-10}$ aryl phosphate) or an adamantylbis, tris or tetrakis(di $C_{6-10}$ aryl phosphoramide).

11. A phosphorus-containing compound according to claim 7, wherein a compound represented by the formula (Ia) is adamantylbis(diphenylphosphate), dimethyladamantylbis(diphenylphosphate), or adamantyltris(diphenyl phosphate).

12. A phosphorus-containing compound according to claim 1, wherein a compound of the formula (I) is represented by the following formula (Ib):

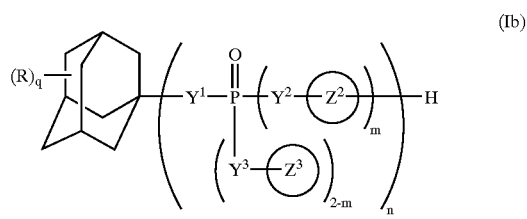

wherein the $Z^2$, $Z^3$, R, $Y^1$, $Y^2$, $Y^3$, m, n and q have the same meanings as defined above.

13. A phosphorus-containing compound according to claim 12, wherein, in the formula (Ib), $Z^2$ and $Z^3$ are the same or different, each representing a benzene ring or an adamantane ring in which these rings may have a substituent; R is a halogen atom, a hydroxyl group, a $C_{1-6}$ alkyl group, or a $C_{1-6}$ alkoxy group; $Y^1$, $Y^2$ and $Y^3$ are the same or different, each representing —O— or —NR$^1$— wherein R$^1$ represents a hydrogen atom or a $C_{1-4}$ alkyl group; and q is an integer of 0 to 4.

14. A phosphorus-containing compound according to claim 12, wherein, in the formula (Ib), R is a hydroxyl group, a $C_{1-4}$ alkyl group, or a $C_{1-4}$ alkoxy group, and q is an integer of 0 to 2.

15. A phosphorus-containing compound according to claim 12, wherein a compound represented by the formula (Ib) is an adamantyl di $C_{6-10}$ arylphosphate or a diadamantyl $C_{6-10}$ arylphosphate.

16. A phosphorus-containing compound according to claim 12, wherein a compound represented by the formula (Ib) is adamantyldiphenylphosphate, dimethyladamantyl diphenylphosphate, or bis(adamantyl)phenylphosphate.

17. A phosphorus-containing compound according to claim 1, wherein a compound of the formula (I) is represented by the following formula (Ic):

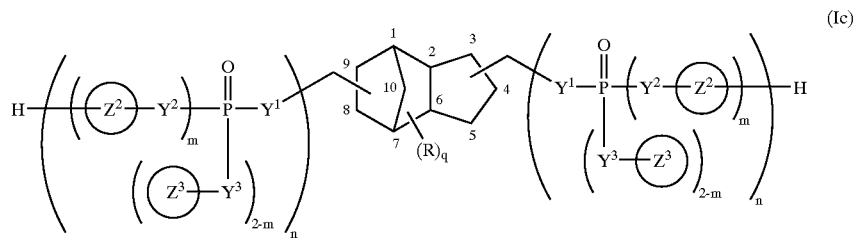

wherein the $Z^2$, $Z^3$, $Y^1$, $Y^2$, $Y^3$, m, n and q have the same meanings as defined above.

18. A phosphorus-containing compound according to claim 17, wherein, in the formula (Ic), $Z^2$ and $Z^3$ each is a benzene ring which may have a substituent; R is a halogen atom, a hydroxyl group, a $C_{1-6}$alkyl group, or a $C_{1-6}$ alkoxy group; and $Y^1$, $Y^2$ and $Y^3$ are —O—.

19. A phosphorus-containing compound according to claim 17, wherein a compound represented by the formula (Ic) is bis[(di $C_{6-10}$ arylphosphoroxy)methyl]tricyclo [5.2.1.0$^{2,6}$]decane.

20. A phosphorus-containing compound according to claim 17, wherein a compound represented by the formula (Ic) is bis[(diphenylphosphoroxy)methyl]tricyclo[5.2.1.0$^{2,6}$] decane.

21. A phosphorus-containing compound according to claim 17, wherein a compound represented by the formula (Ic) is (4R,8S)-bis(diphenylphosphoroxymethyl)-(1R,2S, 6R,7R)-tricyclo[5.2.1.0$^{2,6}$]decane.

22. A phosphorus-containing compound according to claim 1, wherein a compound of the formula (I) is represented by the following formula (Id):

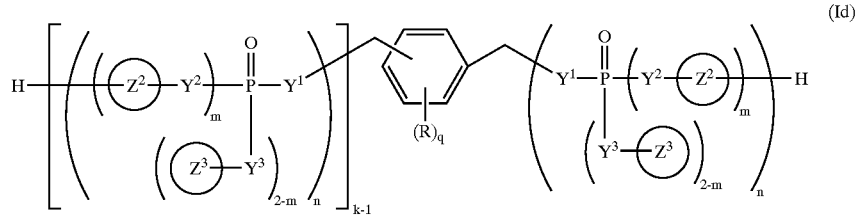

wherein the $Z^2$, $Z^3$, R, $Y^1$, $Y^2$, $Y^3$, m, n and q have the same meanings as defined above.

23. A phosphorus-containing compound according to claim 22, wherein, in the formula (Id), $Z^2$ and $Z^3$ each is a benzene ring which may have a substituent; and $Y^1$, $Y^2$ and $Y^3$ are —O—.

24. A phosphorus-containing compound according to claim 22, wherein a compound represented by the formula (Id) is xylyleneglycolbis(diphenylphosphate).

25. A phosphorus-containing compound according to claim 1, wherein a compound of the formula (I) or (II) is represented by the following formula (Ie) or (IIa):

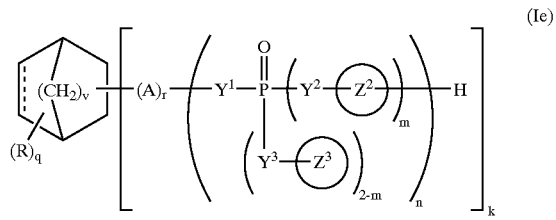

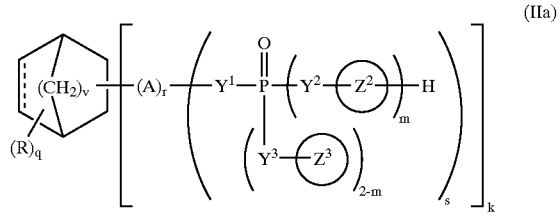

wherein the following structure

———
----- means a single bond or a double bond, v is an integer of 0 to 2; and $Z^2$, $Z^3$, R, A, $Y^1$, $Y^2$, $Y^3$, m, n, q, r and s have the same meanings as defined above.

26. A phosphorus-containing compound according to claim 25, wherein, in the formula (Ie) or (IIa), $Z^2$ and $Z^3$ each is a benzene ring which may have a substituent; R is a halogen atom, a hydroxyl group, a $C_{1-6}$alkyl group which may have a substituent, a $C_{1-6}$ alkoxy group which may have a substituent, or an alkenyl group which may have a substituent; and $Y^1$, $Y^2$ and $Y^3$ are —O—.

27. A phosphorus-containing compound according to claim 25, wherein, in the formula (Ie), n is 1; q is an integer of 0 to 2; r is 1; and s is an integer of 1 to 2.

28. A phosphorus-containing compound according to claim 25, wherein a compound represented by the formula (Ie) or (IIa) is bis(diphenylphosphoroxy)norbornane; bis (diphenylphosphoroxy $C_{1-4}$ alkyl)norbornane; bis (diphenylphosphoroxy)-4-$C_{2-4}$ alkenylcyclohexane; (diphenylphosphoroxy $C_{1-4}$ alkyl)cyclohexene; mono, di or tri-$C_{1-4}$alkyl(diphenylphosphoroxy $C_{1-4}$ alkyl)cyclohexyl phosphate; or bis(diphenylphosphoroxy)-[bis(diphenyl phosphoroxy)$C_{1-4}$alkyl]cyclohexane.

29. A phosphorus-containing compound according to claim 25, wherein a compound represented by the formula (Ie) or (IIa) is 2,3-bis(diphenylphosphoroxy)norbornane, 2,5-bis(diphenylphosphoroxymethyl)norbornane, 1,2-bis (diphenylphosphoroxy)-4-vinylcyclohexane, 1-diphenyl phosphoroxymethyl-3-cyclohexene, 3,3,-dimethyl-5-(diphenylphosphoroxymethyl)cyclohexyl phosphate, or 1,2-bis(diphenylphosphoroxy)-4-[1',2'-bis(diphenyl phosphoroxy)ethyl]cyclohexane.

30. A phosphorus-containing compound according to claim 25, wherein a compound of the formula (Ie) is represented by the following formula (If):

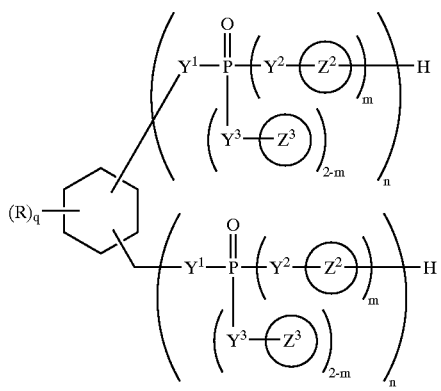

(If)

wherein $Z^2$, $Z^3$, R, $Y^1$, $Y^2$, $Y^3$, m, n and q have the same meanings as defined above.

31. A phosphorus-containing compound according to claim 30, wherein, in the formula (If), $Z^2$ and $Z^3$ are the same or different, each representing a benzene ring; R is a halogen atom, a hydroxyl group, a $C_{1-6}$alkyl group, or a $C_{1-6}$ alkoxy group; and $Y^1$, $Y^2$ and $Y^3$ are the same or different, each representing —O— or —$NR^1$—.

32. A phosphorus-containing compound according to claim 30, wherein a compound represented by the formula (If) is 1-diphenylphosphoroxy-3-diphenylphosphoroxy methylcyclohexane or 3,3,-dimethyl-5-(diphenyl phosphoroxymethyl)cyclohexylphosophate.

33. A phosphorus-containing compound according to claim 1, wherein a compound of the formula (III) is represented by the following formula (IIIa):

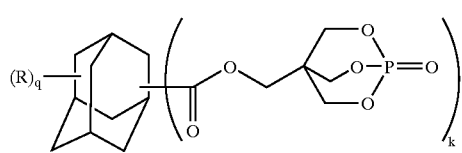

(IIIa)

wherein R, q and k have the same meanings as defined above.

34. A phosphorus-containing compound according to claim 33, wherein, in the formula (IIIa), R is a carboxyl group, a halocarboxyl group, or a $C_{1-4}$alkyl group.

35. A process for producing a phosphorus-containing compound represented by the formula (I), (II) or (III) recited in claim 1, which comprises reacting a compound represented by the following formula (I-1), (II-1) or (III-1) with a compound represented by the following formula (I-2), (II-2) or (III-2):

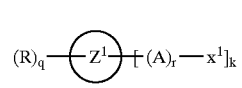

(I-1)

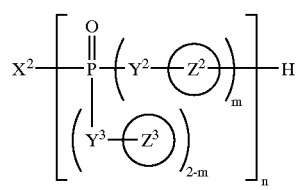

(I-2)

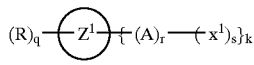

(II-1)

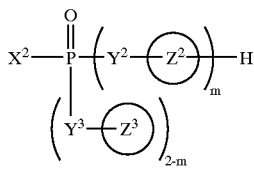

(II-2)

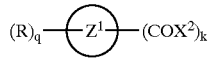

(III-1)

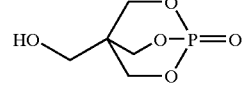

(III-2)

wherein $X^1$ represents a hydroxyl group, a thiol group, an amino group, or a substituted amino group; $X^2$ represents a halogen atom, a hydroxyl group, or an alkoxy group; and the $Z^1$, $Z^2$, R, $Y^1$, $Y^2$, $Y^3$, k, m, q, r and s have the same meanings as defined above.

* * * * *